(12) United States Patent
Tai et al.

(10) Patent No.: US 10,583,140 B2
(45) Date of Patent: Mar. 10, 2020

(54) INGENOL ANALOGS, PHARMACEUTICAL COMPOSITIONS AND METHODS OF USE THEREOF

(71) Applicant: GlaxoSmithKline Intellectual Property Development Limited, Brentford, Middlesex (GB)

(72) Inventors: Vincent Wing-Fai Tai, Research Triangle Park, NC (US); Jun Tang, Research Triangle Park, NC (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/072,278

(22) PCT Filed: Jan. 27, 2017

(86) PCT No.: PCT/IB2017/050452
§ 371 (c)(1),
(2) Date: Jul. 24, 2018

(87) PCT Pub. No.: WO2017/130156
PCT Pub. Date: Aug. 3, 2017

(65) Prior Publication Data
US 2019/0030029 A1 Jan. 31, 2019

Related U.S. Application Data

(60) Provisional application No. 62/287,466, filed on Jan. 27, 2016.

(51) Int. Cl.
| | | |
|---|---|---|
| *A61K 31/506* | (2006.01) |
| *A61K 31/404* | (2006.01) |
| *A61K 31/4035* | (2006.01) |
| *A61K 31/325* | (2006.01) |
| *A61K 31/122* | (2006.01) |
| *A61K 9/16* | (2006.01) |
| *A61K 9/20* | (2006.01) |
| *A61P 31/18* | (2006.01) |

(52) U.S. Cl.
CPC .............. *A61K 31/506* (2013.01); *A61K 9/16* (2013.01); *A61K 9/20* (2013.01); *A61K 31/122* (2013.01); *A61K 31/325* (2013.01); *A61K 31/404* (2013.01); *A61K 31/4035* (2013.01); *A61P 31/18* (2018.01)

(58) Field of Classification Search
CPC .............. A61K 31/122; A61K 31/325; A61K 31/4035; A61K 31/404; A61K 31/506; A61K 9/16; A61K 9/20; A61P 31/18; C07C 2603/86; C07C 271/10; C07C 271/12; C07C 271/24; C07C 271/38; C07C 49/553; C07C 49/727; C07D 209/48
See application file for complete search history.

(56) References Cited

U.S. PATENT DOCUMENTS

2015/0030638 A1* 1/2015 Pianowski ............. A61K 31/22
424/283.1

OTHER PUBLICATIONS

Appendino, Giovanni, et al."Synthesis of modified ingenol esters" European Journal of Organic Chemistry; 1999; pp. 3413-3420; vol. 12.
Sorg, Bernd et al, "On the chemistry of ingenol. III. Synthesis of 3-deoxy-3-oxoingenol and its C-5 esters, and synthesis of ethers and acetals of ingenol." Zeitschrift Fuer Naturforschung, Teil B: Anorganische Chemie, Organische Chemie; 1982; pp. 1640-1647; vol. 37b(12).

* cited by examiner

*Primary Examiner* — Erich A Leeser
(74) *Attorney, Agent, or Firm* — Robert J. Smith

(57) ABSTRACT

The invention relates to compounds of Formula (I), (II), (III) or (IV), salts thereof, pharmaceutical compositions thereof, as well as methods of treating, curing or preventing HIV in subjects.

13 Claims, No Drawings

INGENOL ANALOGS, PHARMACEUTICAL COMPOSITIONS AND METHODS OF USE THEREOF

CROSS-REFERENCE TO RELATED APPLICATIONS

This application is filed pursuant to 35 U.S.C. § 371 as a United States National Phase Application of International Application No. PCT/IB2017/050452 filed Jan. 27, 2017 which claims priority from U.S.62/287,466 filed Jan. 27, 2016.

FIELD OF THE INVENTION

The present invention relates to compounds, pharmaceutical compositions, and methods of use thereof in connection with individuals infected with HIV.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required due to a number of issues including, but not limited to undesirable drug-drug interactions; drug-food interactions; non-adherence to therapy; drug resistance due to mutation of the enzyme target; and inflammation related to the immunologic damage caused by the HIV infection.

Currently, almost all HIV positive patients are treated with therapeutic regimens of antiretroviral drug combinations termed, highly active antiretroviral therapy ("HAART").

However, HAART therapies are often complex because a combination of different drugs must be administered often daily to the patient to avoid the rapid emergence of drug-resistant HIV-1 variants. Despite the positive impact of HAART on patient survival, drug resistance can still occur and the survival and quality of life are not normalized as compared to uninfected persons [Lohse Ann Intern Med 2007 146; 87-95]. Indeed, the incidence of several non-AIDS morbidities and mortalities, such as cardiovascular disease, frailty, and neurocognitive impairment, are increased in HAART-suppressed, HIV-infected subjects [Deeks Annu Rev Med 2011; 62:141-155]. This increased incidence of non-AIDS morbidity/mortality occurs in the context of, and is potentially caused by, elevated systemic inflammation related to the immunologic damage caused by HIV infection [Hunt J Infect Dis 2014][Byakagwa J Infect Dis 2014][Tenorio J Infect Dis 2014].

Modern antiretroviral therapy (ART) has the ability to effectively suppress HIV replication and improve health outcomes for HIV-infected persons, but is believed to not be capable of completely eliminating HIV viral reservoirs within the individual. HIV genomes can remain latent within mostly immune cells in the infected individual and may reactivate at any time, such that after interruption of ART, virus replication typically resumes within weeks. In a handful of individuals, the size of this viral reservoir has been significantly reduced and upon cessation of ART, the rebound of viral replication has been delayed [Henrich T J J Infect Dis 2013][Henrich T J Ann Intern Med 2014]. In one case, the viral reservoir was eliminated during treatment of leukemia and no viral rebound was observed during several years of followup [Hutter G N Engl J Med 2009]. These examples suggest the concept that reduction or elimination of the viral reservoir may be possible and can lead to viral remission or cure. As such, ways have been pursued to eliminate the viral reservoir, by direct molecular means, including excision of viral genomes with CRISPR/Cas9 systems, or to induce reactivation of the latent reservoir during ART so that the latent cells are eliminated. Induction of the latent reservoir typically results in either direct death of the latently infected cell or killing of the induced cell by the immune system after the virus is made visible. As this is performed during ART, viral genomes produced are believed to not result in the infection of new cells and the size of the reservoir may decay.

Reactivation of latent HIV is believed to be achieved by several means, typically by broad and potent mechanisms of cellular activation. These reactivators can be specific to certain cell types, such as anti-CD3/anti-CD28 antibodies that will specifically target T cells, or can be non-specific, such as protein kinase C (PKC) agonists that can activate many cell types. PKC agonists have been described as effective at reactivating latent HIV. Several PKC agonists derived from plants and sponges have been described, including phorbol esters, bryostatin, englerin A, and ingenol.

Ingenol is a diterpenoid compound isolated from plant material derived from representatives of the of *Euphorbia* genus (e.g., sap or seeds of *E. peplus*, dried roots of *E. kansui* or *E. pekinensis*). *E. peplus* sap containing ingenols and other diterpenoids is a traditional medicine for use in skin diseases, including skin cancer, hence the nickname cancer weed. Similarly, *E. kansui* or *E. pekinensis* root are used in traditional Chinese medicine to treat malignancies such as leukemia, purging fluids, or inducing diarrhea. While ingenol is not the only active agent in *Euphorbia* extracts, it is believed to be among the more potent. A derivative of ingenol, ingenol mebutate, is licensed for clinical use in the USA under the trade name Picato® for the treatment of actinic keratosis.

WO 2012/085189, WO 2012/83954 and WO 2012/083953 describe derivates of 3-acyl-ingenol, 3-O-acyl-ingenol, as well as 3-O-carbamoyl-ingenol, which may be useful for the treatment of conditions which are affected by induction of cell death by cytotoxicity or induction of apoptosis and/or by an immunostimulatory effect.

WO 2013/126980 describes the use of certain ingenol derivatives as HIV reactivators of latent HIV virus in viral reservoirs.

WO 2014/001215 describes derivatives of 3-O-heteroaryl-ingenol useful for the treatment of conditions which are affected by induction of cell death by cytotoxicity or induction of apoptosis and/or by an immunostimulatory effect.

Notwithstanding the above, there remains a need for compounds which may possess a desirable combination of potency, limited cytotoxicity, and chemical properties for development as a therapy for HIV.

SUMMARY OF THE INVENTION

In one aspect, the invention provides a compound of the structure according to formula (I):

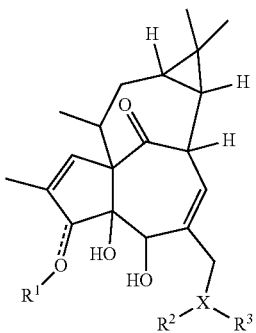

(I)

or a pharmaceutically acceptable salt thereof, wherein:

X is selected from O or N, wherein when X is O, then $R^3$ is absent;

$R^1$ is optionally present, and when present, is selected from the group consisting of —H, —C(O)$R^4$, ($C_2$-$C_9$)heterocycle, and ($C_2$-$C_9$)heteroaryl, wherein the heterocycle and the heteroaryl groups are optionally substituted with one or more $R^{11}$;

$R^2$ and $R^3$ are independently selected from the group consisting of —H, ($C_1$-$C_6$)alkyl, —C(O)$R^{10}$, —C(O)N($R^6$)$_2$, —C(O)O$R^6$, —S(O)$_2R^5$, ($C_2$-$C_9$)heterocycle, and ($C_2$-$C_9$)heteroaryl, wherein when X is N, then $R^2$ and $R^3$ may be taken together to form an $R^2$ and $R^3$ cyclic group selected from ($C_2$-$C_9$)heterocycle or ($C_2$-$C_9$)heteroaryl, and wherein the $R^2$ and $R^3$ cyclic group may be optionally substituted by one or more $R^{12}$;

$R^4$ is selected from the group consisting of —N($R^6$) $R^7$ and ($C_3$-$C_{12}$)cycloalkyl, wherein the cycloalkyl may be optionally substituted with one or more $R^5$;

$R^5$ is ($C_1$-$C_6$)alkyl;

$R^6$ is independently selected from the group consisting of —H and ($C_1$-$C_6$)alkyl;

$R^7$ is selected from the group consisting of aryl and ($C_3$-$C_{12}$)cycloalkyl, wherein the aryl and the cycloalkyl groups are optionally substituted with one or more $R^{13}$;

$R^{10}$ is selected from the group consisting of ($C_1$-$C_6$)alkyl, ($C_3$-$C_{12}$)cycloalkyl, ($C_2$-$C_9$)heterocycle, ($C_2$-$C_9$)heteroaryl, and aryl, wherein the heterocycle and the heteroaryl groups are optionally substituted with one or more $R^{11}$; and wherein $R^{11}$, $R^{12}$ and $R^{13}$ are independently selected from the group consisting of ($C_1$-$C_6$)alkyl, ($C_1$-$C_6$)alkoxy, halo, oxo, haloalkyl, bihaloalkyl, trihaloalkyl, haloalkoxy, bihaloalkoxy, trihaloalkoxy, hydroxyl, amino, and amide.

with the proviso that when X is O and $R^2$ is H, $R^1$ is not present.

In another aspect, the invention provides a compound of the structure according to formula (I) or a pharmaceutically acceptable salt thereof, wherein:

X is selected from O or N, wherein when X is O, then $R^3$ is absent;

$R^1$ is optionally present, and when present, is selected from the group consisting of —H, —C(O)$R^4$, ($C_6$)heterocycle and ($C_9$)heteroaryl, wherein the ($C_6$)heterocycle and the ($C_9$) heteroaryl groups are optionally substituted with one or more $R^{11}$;

$R^2$ and $R^3$ are independently selected from the group consisting of —H, methyl, —C(O)$R^{10}$, —C(O)N($R^6$)$_2$, —S(O)$_2$CH$_3$, ($C_6$)heteroaryl and ($C_9$)heteroaryl, wherein when X is N, then $R^2$ and $R^3$ may be taken together to form a pyrrolidine group optionally substituted by one or more $R^{12}$;

$R^4$ is selected from the group consisting of —N($R^6$) $R^7$ and cyclohexyl, wherein the cyclohexyl may be optionally substituted with methyl;

$R^6$ is methyl;

$R^7$ is phenyl optionally substituted with one or more $R^{13}$;

$R^{10}$ is selected from the group consisting of ($C_1$-$C_4$)alkyl, ($C_3$-$C_9$)cyclohexyl, ($C_5$-$C_6$)heterocycle, and phenyl, wherein the ($C_3$-$C_9$)cyclohexyl, ($C_5$-$C_6$) heterocycle and phenyl are optionally substituted with one or more $R^{11}$; and wherein $R^{11}$, $R^{12}$ and $R^{13}$ are independently selected from the group consisting of methyl, methoxy, oxo, trifluoromethyl and chloro;

with the proviso that when X is O and $R^2$ is H, $R^1$ is not present.

In another aspect, the invention provides a compound according to formula (II):

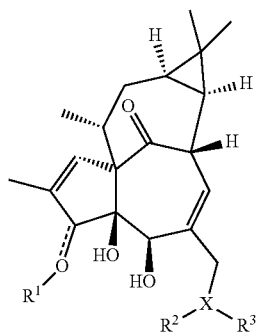

(II)

or a pharmaceutically acceptable salt thereof, wherein:

X is selected from O or N, wherein when X is O, then $R^3$ is absent;

$R^1$ is optionally present, and when present, the group:

is represented as:

$R_1$ is selected from the group consisting of —H, —C(O)$R^4$, ($C_2$-$C_9$)heterocycle, and ($C_2$-$C_9$)heteroaryl, wherein the heterocycle and the heteroaryl groups are optionally substituted with one or more $R^{11}$;

$R^2$ and $R^3$ are independently selected from the group consisting of —H, ($C_1$-$C_6$)alkyl, —C(O)$R^{10}$, —C(O)N($R^6$)$_2$, —C(O)O$R^6$, —S(O)$_2R^5$, ($C_2$-$C_9$)heterocycle, and ($C_2$-$C_9$)heteroaryl, wherein when X is N, then $R^2$ and $R^3$ may be taken together to form a cyclic group selected from ($C_2$-$C_9$)heterocycle or ($C_2$-$C_9$)heteroaryl, and wherein the $R^2$ and $R^3$ cyclic group may be optionally substituted by one or more $R^{12}$;

$R^4$ is selected from the group consisting of —N($R^6$) $R^7$ and ($C_3$-$C_{12}$)cycloalkyl, wherein the cycloalkyl may be optionally substituted with one or more $R^5$;

R⁵ is (C₁-C₆)alkyl;

R⁶ is selected from the group consisting of —H and (C₁-C₆)alkyl;

R⁷ is selected from the group consisting of aryl and (C₃-C₁₂)cycloalkyl, wherein the aryl and the cycloalkyl groups are optionally substituted with one or more R¹³;

R¹⁰ is selected from the group consisting of (C₁-C₆)alkyl, (C₃-C₁₂)cycloalkyl, (C₂-C₆)heterocycle, (C₂-C₉)heteroaryl, and aryl, wherein the heterocycle and the heteroaryl groups are optionally substituted with one or more R¹¹; and wherein R¹¹, R¹² and R¹³ are independently selected from the group consisting of (C₁-C₆)alkyl, (C₁-C₆)alkoxy, halo, oxo, haloalkyl, bihaloalkyl, trihaloalkyl, haloalkoxy, bihaloalkoxy, trihaloalkoxy, hydroxyl, amino, and amide;

with the proviso that when X is O and R² is H, R¹ is not present.

In another aspect, the invention provides a compound according to formula (II):

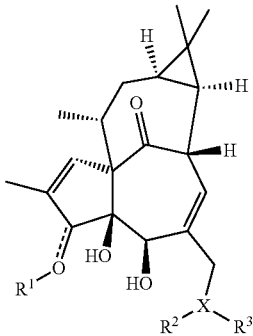

(II)

or a pharmaceutically acceptable salt thereof; wherein

X is selected from O or N, wherein when X is O, then R³ is absent;

R¹ is optionally present, and when present, the group:

is represented as:

and R₁ is selected from the group consisting of —H, —C(O)R⁴, (C₆)heterocycle and (C₉)heteroaryl, wherein the (C₆)heterocycle and the (C₉)heteroaryl groups are optionally substituted with one or more R¹¹;

R² and R³ are independently selected from the group consisting of —H, methyl, —C(O)R¹⁰, —C(O)N(R⁶)₂, —S(O)₂CH₃, (C₆)heteroaryl, and (C₉)heteroaryl, wherein when X is N, then R² and R³ may be taken together to form a pyrrolidine group, optionally substituted by one or more R¹²;

R⁴ is selected from the group consisting of —N(R⁶)R⁷ and cyclohexyl, wherein the cyclohexyl may be optionally substituted with methyl;

R⁶ is methyl;

R⁷ is phenyl, optionally substituted with one or more R¹³;

R¹⁰ is selected from the group consisting of (C₁-C₄)alkyl, (C₃-C₉)cyclohexyl, (C₅-C₆)heterocycle, and phenyl, wherein the (C₃-C₉)cyclohexyl, (C₅-C₆)heterocycle and phenyl are optionally substituted with one or more R¹; and wherein R¹, R¹² and R¹³ are independently selected from the group consisting of methyl, methoxy, oxo, trifluoromethyl and chloro;

with the proviso that when X is O and R² is H, R¹ is not present.

In another aspect, the invention provides a compound of the structure according to formula (II) or a pharmaceutically acceptable salt thereof, wherein:

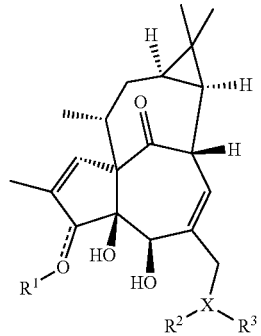

(II)

X is selected from O or N, wherein when X is O, then R³ is absent;

R¹ is optionally present, and when present, is selected from the group consisting of —H and —C(O)R⁴, and wherein the group:

is represented as:

R² and R³ are independently selected from the group consisting of —H, —C(O)R¹⁰, and —C(O)N(R⁶)(R⁷) and wherein when X is N, then R² and R³ may be taken together to form 1,3-dioxoisoindolin-2-yl;

R⁴ is

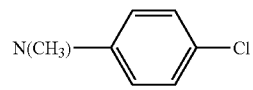

R⁶ and R⁷ are independently selected from methyl and 4-chlorophenyl;

R¹⁰ is selected from the group consisting of methyl and phenyl; and with the proviso that when X is O and R² is H, R¹ is not present.

In another aspect, the invention provides a compound of the structure according to formula (III):

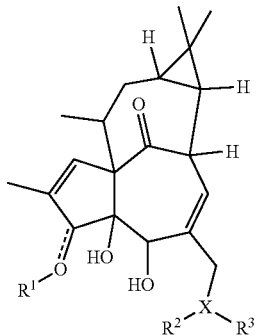

(III)

or a pharmaceutically acceptable salt thereof, wherein:
X is selected from O or N, wherein when X is O, then $R^3$ is absent;
$R^1$ is optionally present, and when present, is selected from the group consisting of —H, C(O)$R^4$, ($C_5$-$C_{12}$) aryl, ($C_3$-$C_{12}$)cycloalkyl, ($C_2$-$C_{12}$)heterocycle, and ($C_2$-$C_{12}$)heteroaryl;
$R^2$ and $R^3$ are independently selected from the group consisting of —H, ($C_1$-$C_6$)alkyl, —C(O)$R^{10}$, —C(O)N($R^{6a}$)($R^{6b}$), —C(O)O$R^{6c}$, —S(O)$_2R^5$, ($C_2$-$C_{12}$)heterocycle, ($C_5$-$C_{12}$) aryl, ($C_3$-$C_{12}$)cycloalkyl and ($C_{2-12}$)heteroaryl, wherein when X is N, then $R^2$ and $R^3$ may be taken together with X to form a ring structure selected from ($C_2$-$C_{12}$)heterocycle or ($C_2$-$C_{12}$)heteroaryl;
$R^4$ is selected from —N($R^6$)($R^7$) or ($C_3$-$C_{12}$)cycloalkyl, or wherein $R^6$ and $R^7$ may be taken together to form a ring structure selected from the group consisting of ($C_2$-$C_{12}$)heterocycle and ($C_2$-$C_{12}$)heteroaryl;
$R^5$, $R^6$, $R^{6a}$, $R^{6b}$, $R^6$, $R^7$ and $R^{10}$ are each independently selected from the group consisting of —H, ($C_1$-$C_6$)alkyl, ($C_5$-$C_{12}$)aryl, ($C_1$-$C_6$)alkoxy, ($C_2$-$C_{12}$)heterocycle, ($C_3$-$C_{12}$) cycloalkyl, ($C_2$-$C_{12}$)heteroaryl and —($C_1$-$C_6$)alkyl-$R^{14}$; wherein $R^{14}$ may be ($C_5$-$C_{12}$)aryl, ($C_2$-$C_{12}$)heteroaryl, ($C_3$-$C_{12}$)cycloalkyl or ($C_2$-$C_{12}$)heterocycle; or wherein when, $R_2$ or $R_3$ is —C(O)N($R^{6a}$)($R^{6b}$), $R^{6a}$ and $R^{6b}$ may together form a ($C_2$-$C_{12}$) heteroaryl or a ($C_2$-$C_{12}$) heterocycle; and
with the proviso that when X is O and $R^2$ is —H, $R^1$ is not present.

In another aspect, the invention provides a compound of the structure according to formula (IV):

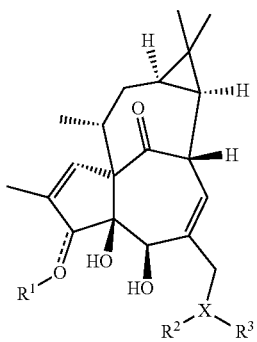

(IV)

or a pharmaceutically acceptable salt thereof, wherein:
X is selected from O or N, wherein when X is O, then $R^3$ is absent;
$R^1$ is optionally present, and when present, is selected from the group consisting of —H, C(O)$R^4$, ($C_5$-$C_{12}$)aryl, ($C_3$-$C_{12}$)cycloalkyl, ($C_2$-$C_{12}$)heterocycle, and ($C_2$-$C_{12}$)heteroaryl, and the group:

is represented as:

$R^2$ and $R^3$ are independently selected from the group consisting of —H, ($C_1$-$C_6$)alkyl, —C(O)$R^{10}$, —C(O)N($R^{6a}$) ($R^{6b}$), —C(O)O$R^{6c}$, —S(O)$_2R^5$, ($C_2$-$C_{12}$)heterocycle, ($C_5$-$C_{12}$) aryl, ($C_3$-$C_{12}$)cycloalkyl and ($C_{2-12}$)heteroaryl, wherein when X is N, then $R^2$ and $R^3$ may be taken together with X to form a ring structure selected from ($C_2$-$C_{12}$)heterocycle or ($C_2$-$C_{12}$)heteroaryl;
$R^4$ is selected from —N($R^6$)($R^7$) or ($C_3$-$C_{12}$)cycloalkyl, or wherein $R^6$ and $R^7$ may be taken together to form a ring structure selected from the group consisting of ($C_2$-$C_{12}$)heterocycle and ($C_2$-$C_{12}$)heteroaryl;
$R^5$, $R^6$, $R^{6a}$, $R^{6b}$, $R^6$, $R^7$ and $R^{10}$ are each independently selected from the group consisting of —H, ($C_1$-$C_6$)alkyl, ($C_5$-$C_{12}$)aryl, ($C_1$-$C_6$)alkoxy, ($C_2$-$C_{12}$)heterocycle, ($C_3$-$C_{12}$) cycloalkyl, ($C_2$-$C_{12}$)heteroaryl and —($C_1$-$C_6$)alkyl-$R^{14}$; wherein $R^{14}$ may be ($C_5$-$C_{12}$)aryl, ($C_2$-$C_{12}$)heteroaryl, ($C_3$-$C_{12}$)cycloalkyl or ($C_2$-$C_{12}$)heterocycle; or wherein when, $R_2$ or $R_3$ is —C(O)N($R^{6a}$)($R^{6b}$), $R^{6a}$ and $R^{6b}$ may together form a ($C_2$-$C_{12}$) heteroaryl or a ($C_2$-$C_{12}$) heterocycle; and
with the proviso that when X is O and $R^2$ is —H, $R^1$ is not present.

In another aspect, the invention provides a pharmaceutical composition comprising a compound according to Formula (I), (II), (III) or (IV) and a pharmaceutically acceptable excipient.

In another aspect, the invention provides a method of curing, treating or preventing an HIV infection in a subject comprising administering to the subject a compound of Formula (I), (II), (III) or (IV) or a pharmaceutically acceptable salt thereof.

These and other aspects are encompassed by the invention as set forth herein.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention. It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to a monovalent saturated aliphatic hydrocarbyl group having from 1 to 14 carbon atoms and, in some embodiments, from 1 to 6 carbon atoms. "$(C_x-C_y)$alkyl" refers to alkyl groups having from x to y carbon atoms. The term "alkyl" includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" or "alkylene" refers to divalent saturated aliphatic hydrocarbyl groups having from 1 to 10 carbon atoms and, in some embodiments, from 1 to 6 carbon atoms. "$(C_u-C_v)$alkylene" refers to alkylene groups having from u to v carbon atoms. The alkylene groups include branched and straight chain hydrocarbyl groups. For example, "$(C_1-C_6)$alkylene" is meant to include methylene, ethylene, propylene, 2-methypropylene, dimethylethylene, pentylene, and so forth. As such, the term "propylene" could be exemplified by the following structure:

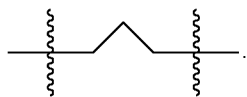

Likewise, the term "dimethylbutylene" could be exemplified by any of the following three structures or more:

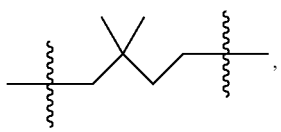 [SMILES: *CCC(C)(C)C*]

p, or

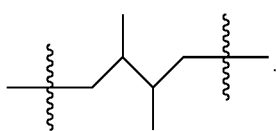 [SMILES: *CC(C)C(C)C*]

Furthermore, the term "$(C_1-C_6)$alkylene" is meant to include such branched chain hydrocarbyl groups as cyclopropylmethylene, which could be exemplified by the following structure:

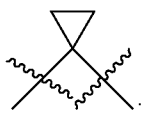

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $(C_x-C_y)$alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, $(C_2-C_6)$alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}C(O)$alkyl, —$NR^{20}C(O)$cycloalkyl, —$NR^{20}C(O)$alkenyl, —$NR^{20}C(O)$alkynyl, —$NR^{20}C(O)$aryl, —$NR^{20}C(O)$heteroaryl, —$NR^{20}C(O)$heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$ where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —$C(O)NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"AUC" refers to the area under the plot of plasma concentration of drug (not logarithm of the concentration) against time after drug administration.

"$EC_{50}$" refers to the concentration of a drug that gives half-maximal response.

"IC$_{50}$" refers to the half-maximal inhibitory concentration of a drug. Sometimes, it is also converted to the pIC$_{50}$ scale (–log IC$_{50}$), in which higher values indicate exponentially greater potency.

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below:

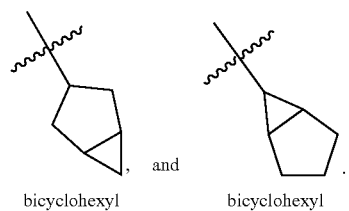 [SMILES: *C1CC2CC2C1 ; *C1C2CCCC12]

bicyclohexyl, and bicyclohexyl.

"(C$_u$-C$_v$)cycloalkyl" refers to cycloalkyl groups having u to v carbon atoms.

"Carboxy" or "carboxyl" refers interchangeably to the groups

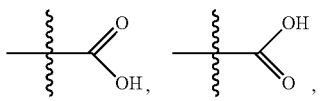

C(O)O, or —CO$_2$.

"Halo" or "halogen" refers to fluoro, chloro, bromo, and iodo.

"Haloalkyl" refers to substitution of an alkyl group with 1 to 3 halo groups (e.g., bihaloalkyl or trihaloalkyl, bifluoromethyl or trifluoromethyl).

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy, bihaloalkoxy, trihaloalkoxy).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., C$_3$-C$_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" or "fused heterocycle" refer to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

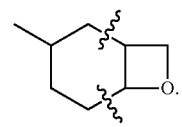

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {N⁺—O⁻} and sulfur such as S(O) and S(O)₂, and the quaternized form of any basic nitrogen.

"Dioxoisoindolin-2-yl" is represented by the structure, which may be optionally substituted:

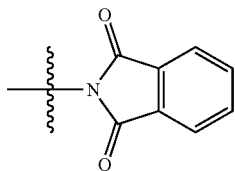 [SMILES: *N1C(=O)c2ccccc2C1=O]

"Pyrrolidine" is represented by the structure which may be optionally substituted

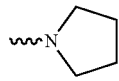

"Oxo" refers to a (=O) group.

"Polymorphism" refers to when two or more clearly different phenotypes exist in the same population of a species where the occurrence of more than one form or morph. In order to be classified as such, morphs must occupy the same habitat at the same time and belong to a panmictic population (one with random mating).

"Protein binding" refers to the binding of a drug to proteins in blood plasma, tissue membranes, red blood cells and other components of blood.

"Protein shift" refers to determining a binding shift by comparing the $EC_{50}$ values determined in the absence and presence of human serum.

"Racemates" refers to a mixture of enantiomers. In an embodiment of the invention, the compounds of Formulas (I), (II), (III) and (IV), or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereo centers. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles. The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002. "Patient" or "subject" refers to mammals and includes humans and non-human mammals.

Cure" or "Curing" a disease in a patient refer to is used to the denote the eradication, stoppage, halt or end of the human immunodeficiency virus or symptoms, or the progression of the symptoms or virus, for a defined period. As an example, in one embodiment, "cure" or "curing" refers to a therapeutic administration or a combination of administrations that alone or in combination with one or more other compounds induces and maintains sustained viral control (undetectable levels of plasma viremia by, e.g., a polymerase chain reaction (PCR) test, a bDNA (branched chain DNA) test or a NASBA (nucleic acid sequence based amplification) test,) of human immunodeficiency virus after a minimum of two years without any other therapeutic intervention. The above PCR, bDNA and NASBA tests are carried out using techniques known and familiar to one skilled in the art. As an example, the eradication, stoppage, halt or end of the human immunodeficiency virus or symptoms, or the progression of the symptoms or virus, may be sustained for a minimum of two years.

Treating" or "treatment" of a disease in a patient refers to 1) preventing the disease from occurring in a patient that is predisposed or does not yet display symptoms of the disease;

2) inhibiting the disease or arresting its development; or 3) ameliorating or causing regression of the disease.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

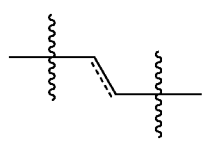

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

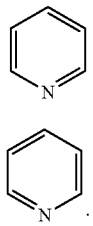

A

B

The present invention includes compounds as well as their pharmaceutically acceptable salts. Accordingly, the word "or" in the context of "a compound or a pharmaceutically acceptable salt thereof" is understood to refer to either: 1) a compound alone or a compound and a pharmaceutically acceptable salt thereof (alternative), or 2) a compound and a pharmaceutically acceptable salt thereof (in combination).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C($R^x$)$_2$", it should be understood that the two $R^x$ groups can be the same, or they can be different if $R^x$ is defined as having more than one possible identity. In addition, certain substituents are drawn as —$R^xR^y$, where the "—" indicates a bond adjacent to the parent molecule and $R^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In accordance with one embodiment of the present invention, there is provided a compound of the structure according to formula (I):

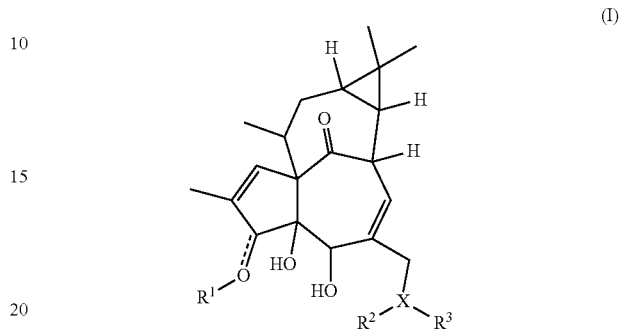

(I)

or a pharmaceutically acceptable salt thereof, wherein:

X is selected from O or N, wherein when X is O, then $R^3$ is absent;

$R^1$ is optionally present, and when present, is selected from the group consisting of —H, —C(O)$R^4$, ($C_2$-$C_9$) heterocycle, and ($C_2$-$C_9$)heteroaryl, wherein the heterocycle and the heteroaryl groups are optionally substituted with one or more $R^{11}$;

$R^2$ and $R^3$ are independently selected from the group consisting of —H, ($C_1$-$C_6$)alkyl, —C(O)$R^{10}$, —C(O) N($R^6$)$_2$, —C(O)O$R^6$, —S(O)$_2R^5$, ($C_2$-$C_9$)heterocycle, and ($C_2$-$C_9$)heteroaryl, wherein when X is N, then $R^2$ and $R^3$ may be taken together to form an $R^2$ and $R^3$ cyclic group selected from ($C_2$-$C_9$)heterocycle or ($C_2$-$C_9$)heteroaryl, and wherein the $R^2$ and $R^3$ cyclic group may be optionally substituted by one or more $R^{12}$;

$R^4$ is selected from the group consisting of —N($R^6$) $R^7$ and ($C_3$-$C_{12}$)cycloalkyl, wherein the cycloalkyl may be optionally substituted with one or more $R^5$;

$R^5$ is ($C_1$-$C_6$)alkyl;

$R^6$ is independently selected from the group consisting of —H and ($C_1$-$C_6$)alkyl;

$R^7$ is selected from the group consisting of aryl and ($C_3$-$C_{12}$)cycloalkyl, wherein the aryl and the cycloalkyl groups are optionally substituted with one or more $R^{13}$;

$R^{10}$ is selected from the group consisting of ($C_1$-$C_6$)alkyl, ($C_3$-$C_{12}$)cycloalkyl, ($C_2$-$C_9$)heterocycle, ($C_2$-$C_9$)heteroaryl, and aryl, wherein the heterocycle and the heteroaryl groups are optionally substituted with one or more $R^{11}$; and wherein $R^{11}$, $R^{12}$ and $R^{13}$ are independently selected from the group consisting of ($C_1$-$C_6$)alkyl, ($C_1$-$C_6$)alkoxy, halo, oxo, haloalkyl, bihaloalkyl, trihaloalkyl, haloalkoxy, bihaloalkoxy, trihaloalkoxy, hydroxyl, amino, and amide.

with the proviso that when X is O and $R^2$ is H, $R^1$ is not present.

In accordance with the present invention, there is provided a compound having the structure of formula (I):

(I)

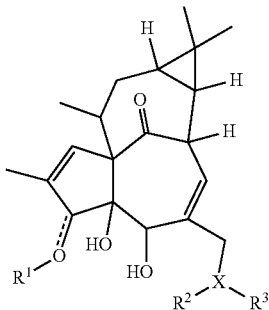

or a pharmaceutically acceptable salt thereof, wherein:

X is selected from O or N, wherein when X is O, then $R^3$ is absent;

$R^1$ is optionally present, and when present, is selected from the group consisting of —H, —C(O)$R^4$, ($C_6$)heterocycle and ($C_9$)heteroaryl, wherein the ($C_6$)heterocycle and the ($C_9$) heteroaryl groups are optionally substituted with one or more $R^{11}$;

$R^2$ and $R^3$ are independently selected from the group consisting of —H, methyl, —C(O)$R^{10}$, —C(O)N($R^6$)$_2$, —S(O)$_2$CH$_3$, ($C_6$)heteroaryl and ($C_9$)heteroaryl, wherein when X is N, then $R^2$ and $R^3$ may be taken together to form a pyrrolidine group optionally substituted by one or more $R^{12}$;

$R^4$ is selected from the group consisting of —N($R^6$) $R^7$ and cyclohexyl, wherein the cyclohexyl may be optionally substituted with methyl;

$R^6$ is methyl;

$R^7$ is phenyl optionally substituted with one or more $R^{13}$;

$R^{10}$ is selected from the group consisting of ($C_1$-$C_4$)alkyl, ($C_3$-$C_9$)cyclohexyl, ($C_5$-$C_6$)heterocycle, and phenyl, wherein the ($C_3$-$C_9$)cyclohexyl, ($C_5$-$C_6$) heterocycle and phenyl are optionally substituted with one or more $R^{11}$; and wherein $R^{11}$, $R^{12}$ and $R^{13}$ are independently selected from the group consisting of methyl, methoxy, oxo, trifluoromethyl and chloro;

with the proviso that when X is O and $R^2$ is H, $R^1$ is not present.

In accordance with one embodiment of the present invention, there is provided a compound according to formula (II):

(II)

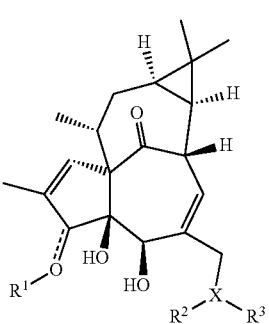

or a pharmaceutically acceptable salt thereof, wherein:

X is selected from O or N, wherein when X is O, then $R^3$ is absent;

$R^1$ is optionally present, and when present, the group:

is represented as:

and $R_1$ is selected from the group consisting of —H, —C(O)$R^4$, ($C_2$-$C_9$)heterocycle, and ($C_2$-$C_9$)heteroaryl, wherein the heterocycle and the heteroaryl groups are optionally substituted with one or more $R^{11}$;

$R^2$ and $R^3$ are independently selected from the group consisting of —H, ($C_1$-$C_6$)alkyl, —C(O)$R^{10}$, —C(O) N($R^6$)$_2$, —C(O)O$R^6$, —S(O)$_2$$R^5$, ($C_2$-$C_9$)heterocycle, and ($C_2$-$C_9$)heteroaryl, wherein when X is N, then $R^2$ and $R^3$ may be taken together to form an $R^2$ and $R^3$ cyclic group selected from ($C_2$-$C_9$)heterocycle or ($C_2$-$C_9$)heteroaryl, and wherein the $R^2$ and $R^3$ cyclic group may be optionally substituted by one or more $R^{12}$;

$R^4$ is selected from the group consisting of —N($R^6$) $R^7$ and ($C_3$-$C_{12}$)cycloalkyl, wherein the cycloalkyl may be optionally substituted with one or more $R^5$;

$R^5$ is ($C_1$-$C_6$)alkyl;

$R^6$ is independently selected from the group consisting of —H and ($C_1$-$C_6$)alkyl;

$R^7$ is selected from the group consisting of aryl and ($C_3$-$C_{12}$)cycloalkyl, wherein the aryl and the cycloalkyl groups are optionally substituted with one or more $R^{13}$;

$R^{10}$ is selected from the group consisting of ($C_1$-$C_6$)alkyl, ($C_3$-$C_{12}$)cycloalkyl, ($C_2$-$C_9$)heterocycle, ($C_2$-$C_9$)heteroaryl, and aryl, wherein the heterocycle and the heteroaryl groups are optionally substituted with one or more $R^{11}$; and wherein $R^{11}$, $R^{12}$ and $R^{13}$ are independently selected from the group consisting of ($C_1$-$C_6$)alkyl, ($C_1$-$C_6$)alkoxy, halo, oxo, haloalkyl, bihaloalkyl, trihaloalkyl, haloalkoxy, bihaloalkoxy, trihaloalkoxy, hydroxyl, amino, and amide.

with the proviso that when X is O and $R^2$ is H, $R^1$ is not present.

In accordance with one embodiment of the present invention, there is a compound according to formula (II):

(II)

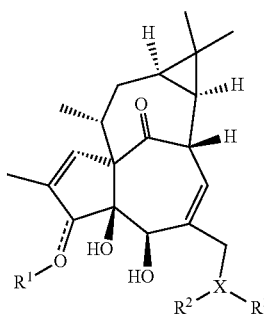

or a pharmaceutically acceptable salt thereof:

X is selected from O or N, wherein when X is O, then $R^3$ is absent;

$R^1$ is optionally present, and when present, the group:

is represented as:

and $R_1$ is selected from the group consisting of —H, —C(O)R$^4$, (C$_6$)heterocycle and (C$_9$)heteroaryl, wherein the (C$_6$)heterocycle and the (C$_9$) heteroaryl groups are optionally substituted with one or more $R^{11}$;

$R^2$ and $R^3$ are independently selected from the group consisting of —H, methyl, —C(O)R$^{10}$, —C(O)N(R$^6$)$_2$, —S(O)$_2$CH$_3$, (C$_6$)heteroaryl and (C$_9$)heteroaryl, wherein when X is N, then $R^2$ and $R^3$ may be taken together to form a pyrrolidine group optionally substituted by one or more $R^{12}$;

$R^4$ is selected from the group consisting of —N(R$^6$) R$^7$ and cyclohexyl, wherein the cyclohexyl may be optionally substituted with methyl;

$R^6$ is methyl;

$R^7$ is phenyl optionally substituted with one or more $R^{13}$;

$R^{10}$ is selected from the group consisting of (C$_1$-C$_4$)alkyl, (C$_3$-C$_9$)cyclohexyl, (C$_5$-C$_6$)heterocycle, and phenyl, wherein the (C$_3$-C$_9$)cyclohexyl, (C$_5$-C$_6$) heterocycle and phenyl are optionally substituted with one or more $R^{11}$; and wherein $R^{11}$, $R^{12}$ and $R^{13}$ are independently selected from the group consisting of methyl, methoxy, oxo, trifluoromethyl and chloro;

with the proviso that when X is O and $R^2$ is H, $R^1$ is not present.

In accordance with one embodiment of the present invention, there is provided a compound of the structure according to formula (II):

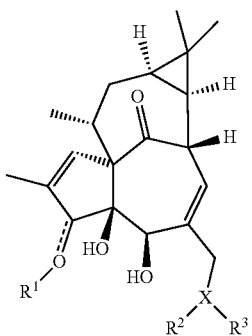

(II)

or a pharmaceutically acceptable salt thereof, wherein:

X is selected from O or N, wherein when X is O, then $R^3$ is absent;

$R^1$ is optionally present, and when present, is selected from the group consisting of —H and —C(O)R$^4$, and wherein the group:

is represented as:

$R^2$ and $R^3$ are independently selected from the group consisting of —H, —C(O)R$^{10}$, and —C(O)N(R$^6$)(R$^7$) and wherein when X is N, then $R^2$ and $R^3$ may be taken together to form 1,3-dioxoisoindolin-2-yl;

$R^4$ is

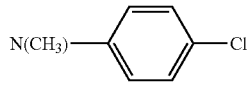

$R^6$ and $R^7$ selected from methyl and 4-chlorophenyl;

$R^{10}$ is selected from the group consisting of methyl and phenyl; and with the proviso that when X is O and $R^2$ is H, $R^1$ is not present.

In accordance with one embodiment of the present invention, there is provided a compound having the structure of formula (I) or formula (II) above, wherein $R^1$ is present and selected from the group consisting of —H and —C(O)R$^4$.

In accordance with one embodiment of the present invention, there is provided a compound having the structure of formula (I) or formula (II) above, wherein $R^1$ is H.

In accordance with one embodiment of the present invention, there is provided a compound having the structure of formula (I) or formula (II) above, wherein $R^1$ is —C(O)R$^4$ and $R^4$ is —N(R$^6$)(R$^7$).

In accordance with one embodiment of the present invention, there is provided a compound having the structure of formula (I) or formula (II) above, wherein $R^6$ is methyl and $R^7$ is aryl (e.g., C$_6$ aryl) substituted by chloro.

In accordance with one embodiment of the present invention, there is provided a compound having the structure of formula (I) or formula (II) above, wherein X is O.

In accordance with one embodiment of the present invention, there is provided a compound having the structure of formula (I) or formula (II) above, wherein $R^2$ is —C(O)R$^{10}$.

In accordance with one embodiment of the present invention, there is provided a compound having the structure of formula (I) or formula (II) above, wherein $R^{10}$ is aryl (e.g., C$_6$ aryl) or methyl.

In accordance with one embodiment of the present invention, there is provided a compound having the structure of formula (I) or formula (II) above, wherein X is N.

In accordance with one embodiment of the present invention, there is provided a compound having the structure of formula (I) or formula (II) above, wherein $R^2$ and $R^3$ together form a (C$_2$-C$_9$)heteroaryl optionally substituted by one or more $R^{12}$.

In accordance with one embodiment of the present invention, there is provided a compound having the structure of formula (I) or formula (II) above, wherein $R^{12}$ is oxo.

In accordance with one embodiment of the present invention, there is provided a compound having the structure of formula (I) or formula (II) above, wherein $R_1$ is absent.

In accordance with one embodiment of the present invention, there is provided a compound having the structure of formula (I) or formula (II) above, wherein X is O and $R_2$ is H.

In accordance with one embodiment of the present invention, there is provided a compound of the structure according to formula (III):

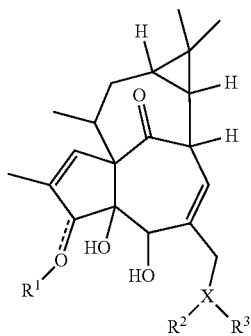

(III)

or a pharmaceutically acceptable salt thereof, wherein:

X is selected from O or N, wherein when X is O, then $R^3$ is absent;

$R^1$ is optionally present, and when present, is selected from the group consisting of —H, C(O)$R^4$, ($C_5$-$C_{12}$)aryl, ($C_3$-$C_{12}$)cycloalkyl, ($C_2$-$C_{12}$)heterocycle, and ($C_2$-$C_{12}$)heteroaryl;

$R^2$ and $R^3$ are independently selected from the group consisting of —H, ($C_1$-$C_6$)alkyl, —C(O)$R^{10}$, —C(O)N($R^{6a}$)($R^{6b}$), —C(O)O$R^{6c}$, —S(O)$_2R^5$, ($C_2$-$C_{12}$)heterocycle, ($C_5$-$C_{12}$)aryl, ($C_3$-$C_{12}$)cycloalkyl and ($C_{2-12}$)heteroaryl, wherein when X is N, then $R^2$ and $R^3$ may be taken together with X to form a ring structure selected from ($C_2$-$C_{12}$)heterocycle or ($C_2$-$C_{12}$)heteroaryl;

$R^4$ is selected from —N($R^6$)($R^7$) or ($C_3$-$C_{12}$)cycloalkyl, or wherein $R^6$ and $R^7$ may be taken together to form a ring structure selected from the group consisting of ($C_2$-$C_{12}$) heterocycle and ($C_2$-$C_{12}$)heteroaryl;

wherein $R^5$, $R^6$, $R^{6a}$, $R^{6b}$, $R^{6c}$, $R^7$ and $R^{10}$ are selected from the group consisting of —H, ($C_1$-$C_6$)alkyl, ($C_5$-$C_{12}$)aryl, ($C_1$-$C_6$)alkoxy, ($C_3$-$C_{12}$)heterocycle, ($C_3$-$C_{12}$)cycloalkyl, ($C_2$-$C_{12}$)heteroaryl and —($C_1$-$C_6$)alkyl-$R^{14}$; wherein $R^{14}$ may be ($C_5$-$C_{12}$)aryl, ($C_2$-$C_{12}$)heteroaryl, ($C_3$-$C_{12}$)cycloalkyl or ($C_2$-$C_{12}$)heterocycle; or wherein when, $R_2$ or $R_3$ is —C(O)N($R^{6a}$)($R^{6b}$), $R^{6a}$ and $R^{6b}$ may together form a ($C_2$-$C_{12}$) heteroaryl or a ($C_2$-$C_{12}$) heterocycle; and with the proviso that when X is O and $R^2$ is —H, $R^1$ is not present.

In accordance with one embodiment of the present invention, there is provided a compound of the structure according to formula (IV):

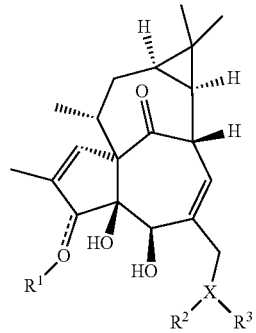

(IV)

or a pharmaceutically acceptable salt thereof, wherein:

X is selected from O or N, wherein when X is O, then $R^3$ is absent;

$R^1$ is optionally present, and when present, is selected from the group consisting of —H, C(O)$R^4$, ($C_5$-$C_{12}$)aryl, ($C_3$-$C_{12}$)cycloalkyl, ($C_2$-$C_{12}$)heterocycle, and ($C_2$-$C_{12}$)heteroaryl; and when present the group:

is represented as:

$R^2$ and $R^3$ are independently selected from the group consisting of —H, ($C_1$-$C_6$)alkyl, —C(O)$R^{10}$, —C(O)N($R^{6a}$)($R^{6b}$), —C(O)O$R^{6c}$, —S(O)$_2R^5$, ($C_2$-$C_{12}$)heterocycle, ($C_5$-$C_{12}$)aryl, ($C_3$-$C_{12}$)cycloalkyl and ($C_{2-12}$)heteroaryl, wherein when X is N, then $R^2$ and $R^3$ may be taken together with X to form a ring structure selected from ($C_2$-$C_{12}$)heterocycle or ($C_2$-$C_{12}$)heteroaryl;

$R^4$ is selected from —N($R^6$)($R^7$) or ($C_3$-$C_{12}$)cycloalkyl, or wherein $R^6$ and $R^7$ may be taken together to form a ring structure selected from the group consisting of ($C_2$-$C_{12}$) heterocycle and ($C_2$-$C_{12}$)heteroaryl;

wherein $R^5$, $R^6$, $R^{6a}$, $R^{6b}$, $R^{6c}$, $R^7$ and $R^{10}$ is selected from the group consisting of —H, ($C_1$-$C_6$)alkyl, ($C_5$-$C_{12}$)aryl, ($C_1$-$C_6$)alkoxy, ($C_3$-$C_{12}$)heterocycle, ($C_3$-$C_{12}$)cycloalkyl, ($C_2$-$C_{12}$)heteroaryl and —($C_1$-$C_6$)alkyl-$R^{14}$; wherein $R^{14}$ may be ($C_5$-$C_{12}$)aryl, ($C_2$-$C_{12}$)heteroaryl, ($C_3$-$C_{12}$)cycloalkyl or ($C_2$-$C_{12}$)heterocycle; or wherein when, $R_2$ or $R_3$ is —C(O)N($R^{6a}$)($R^{6b}$), $R^{6a}$ and $R^{6b}$ may together form a ($C_2$-$C_{12}$) heteroaryl or a ($C_2$-$C_{12}$) heterocycle; and with the proviso that when X is O and $R^2$ is —H, $R^1$ is not present.

In another aspect, the invention provides a compound of the structure according to formula (III):

23

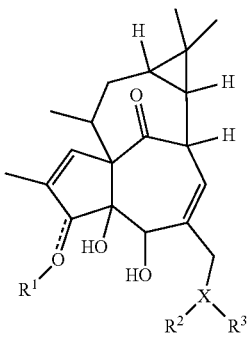

(III)

or a pharmaceutically acceptable salt thereof, wherein:

X is selected from O or N, wherein when X is O, then $R^3$ is absent;

$R^1$ is optionally present, and when present, is selected from the group consisting of —H, $C(O)R^4$, $(C_5-C_{12})$aryl, $(C_3-C_{12})$cycloalkyl, $(C_3-C_{12})$heterocycle, and $(C_3-C_{12})$heteroaryl;

$R^2$ and $R^3$ are independently selected from the group consisting of —H, $(C_1-C_6)$alkyl, —$C(O)R^{10}$, —$C(O)N(R^{6a})(R^{6b})$, —$C(O)OR^{6c}$, —$S(O)_2R^5$, $(C_3-C_{12})$heterocycle, $(C_5-C_{12})$aryl, $(C_3-C_{12})$cycloalkyl and $(C_{3-12})$heteroaryl, wherein when X is N, then $R^2$ and $R^3$ may be taken together with X to form a ring structure selected from $(C_3-C_{12})$heterocycle or $(C_3-C_{12})$heteroaryl;

$R^4$ is selected from —$N(R^6)(R^7)$ or $(C_3-C_{12})$cycloalkyl, or wherein $R^6$ and $R^7$ may be taken together to form a ring structure selected from the group consisting of $(C_3-C_{12})$heterocycle and $(C_3-C_{12})$heteroaryl;

$R^5$, $R^6$, $R^{6a}$, $R^{6b}$, $R^{6c}$, $R^7$ and $R^{10}$ are each independently selected from the group consisting of —H, $(C_1-C_6)$alkyl, $(C_5-C_{12})$aryl, $(C_1-C_6)$alkoxy, $(C_3-C_{12})$heterocycle, $(C_3-C_{12})$cycloalkyl, $(C_3-C_{12})$heteroaryl and —$(C_1-C_6)$alkyl-$R^{14}$; wherein $R^{14}$ may be $(C_5-C_{12})$aryl, $(C_3-C_{12})$heterocycle, $(C_3-C_{12})$cycloalkyl or $(C_3-C_{12})$heterocycle; or wherein when, $R_2$ or $R_3$ is —$C(O)N(R^{6a})(R^{6b})$, $R^{6a}$ and $R^{6b}$ may together form a $(C_3-C_{12})$ heteroaryl or a $(C_3-C_{12})$ heterocycle; and with the proviso that when X is O and $R^2$ is —H, $R^1$ is not present.

In another aspect, the invention provides a compound of the structure according to formula (IV):

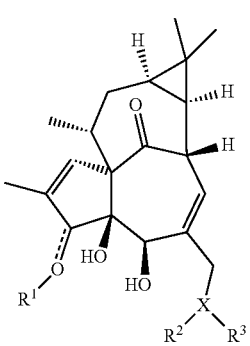

(IV)

or a pharmaceutically acceptable salt thereof, wherein:

X is selected from O or N, wherein when X is O, then $R^3$ is absent;

24

$R^1$ is optionally present, and when present, is selected from the group consisting of —H, $C(O)R^4$, $(C_5-C_{12})$aryl, $(C_3-C_{12})$cycloalkyl, $(C_3-C_{12})$heterocycle, and $(C_3-C_{12})$heteroaryl, and the group:

is represented as:

$R^2$ and $R^3$ are independently selected from the group consisting of —H, $(C_1-C_6)$alkyl, —$C(O)R^{10}$, —$C(O)N(R^{6a})(R^{6b})$, —$C(O)OR^{6c}$, —$S(O)_2R^5$, $(C_3-C_{12})$heterocycle, $(C_5-C_{12})$ aryl, $(C_3-C_{12})$cycloalkyl and $(C_{3-12})$heteroaryl, wherein when X is N, then $R^2$ and $R^3$ may be taken together with X to form a ring structure selected from $(C_3-C_{12})$heterocycle or $(C_3-C_{12})$heteroaryl;

$R^4$ is selected from —$N(R^6)(R^7)$ or $(C_3-C_{12})$cycloalkyl, or wherein $R^6$ and $R^7$ may be taken together to form a ring structure selected from the group consisting of $(C_3-C_{12})$heterocycle and $(C_3-C_{12})$heteroaryl;

$R^5$, $R^6$, $R^{6a}$, $R^{6b}$, $R^{6c}$, $R^7$ and $R^{10}$ are each independently selected from the group consisting of —H, $(C_1-C_6)$alkyl, $(C_5-C_{12})$aryl, $(C_1-C_6)$alkoxy, $(C_3-C_{12})$heterocycle, $(C_3-C_{12})$cycloalkyl, $(C_3-C_{12})$heteroaryl and —$(C_1-C_6)$alkyl-$R^{14}$; wherein $R^{14}$ may be $(C_5-C_{12})$aryl, $(C_3-C_{12})$heterocycle, $(C_3-C_{12})$cycloalkyl or $(C_3-C_{12})$heterocycle; or wherein when, $R_2$ or $R_3$ is —$C(O)N(R^{6a})(R^{6b})$, $R^{6a}$ and $R^{6b}$ may together form a $(C_3-C_{12})$ heteroaryl or a $(C_3-C_{12})$ heterocycle; and with the proviso that when X is O and $R^2$ is —H, $R^1$ is not present In accordance with one embodiment of the present invention, there is provided a compound having the structure of formula (III) or (IV), wherein $R^1$ is present and selected from the group consisting of —H and —$C(O)R^4$.

In accordance with one embodiment of the present invention, there is provided a compound having the structure of formula (III) or (IV), wherein $R^1$ is H.

In accordance with one embodiment of the present invention, there is provided a compound having the structure of formula (III) or (IV), wherein $R^1$ is —$C(O)R^4$ and $R^4$ is —$N(R^6)(R^7)$.

In accordance with one embodiment of the present invention, there is provided a compound having the structure of formula (III) or (IV), wherein when $R^1$ is —$C(O)R^4$ and $R^4$ is —$N(R^6)(R^7)$, $R^6$ is methyl and $R^7$ is $C_6$ aryl substituted by chloro.

In accordance with one embodiment of the present invention, there is provided a compound having the structure of formula (III) or (IV), wherein X is O.

In accordance with one embodiment of the present invention, there is provided a compound having the structure of formula (III) or (IV), wherein $R^2$ is —$C(O)R^{10}$.

In accordance with one embodiment of the present invention, there is provided a compound having the structure of formula (III) or (IV), wherein $R^{10}$ is aryl (e.g., $C_6$ aryl) or methyl.

In accordance with one embodiment of the present invention, there is provided a compound having the structure of formula (III) or (IV), wherein X is N.

In accordance with one embodiment of the present invention, there is provided a compound having the structure of formula (III) or (IV), wherein $R^2$ and $R^3$ together form a $(C_2\text{-}C_{12})$heteroaryl.

In accordance with one embodiment of the present invention, there is provided a compound having the structure of formula (III) or (IV), wherein $R_1$ is absent.

In accordance with one embodiment of the present invention, there is provided a compound having the structure of formula (III) or (IV), wherein X is O and $R_2$ is H.

In accordance with one embodiment of the present invention, there is provided a compound having the structure of formula (III) or (IV), wherein X is O and $R^2$ is —C(O)N$(R^{6a})(R^{6a})$.

In accordance with one embodiment of the present invention, $R^{6a}$ and $R^{6b}$ are selected from the group consisting of —H, $(C_1\text{-}C_6)$alkyl, $(C_5\text{-}C_{12})$aryl, $(C_2\text{-}C_{12})$heteroaryl, $(C_3\text{-}C_{12})$ cycloalkyl, $(C_2\text{-}C_{12})$heterocycle and $(C_1\text{-}C_6)$alkyl-$R^{14}$ wherein $R^{14}$ may be $(C_5\text{-}C_{12})$aryl, $(C_2\text{-}C_{12})$heteroaryl, $(C_3\text{-}C_{12})$ cycloalkyl or $(C_2\text{-}C_{12})$heterocycle, or wherein when $R_2$ or $R_3$ is —C(O)N$(R^6)(R^{6a})$, $R^{6a}$ and $R^{6b}$ may together form a $(C_2\text{-}C_{12})$ heteroaryl or a $(C_2\text{-}C_{12})$ heterocycle.

In accordance with one embodiment of the present invention, $R^{6a}$ and $R^{6b}$ may be selected from the group consisting of H, $(C_4)$alkyl, $(C_6)$aryl, $(C_1)$alkyl-$R^{14}$ wherein $R^{14}$ is $(C_6\text{-}C_9)$aryl or $(C_6)$ cycloalkyl.

In accordance with one embodiment of the present invention, there is provided a compound of formula (II) or (IV), wherein $R^{6a}$ and $R^{6b}$ together form a $(C_2\text{-}C_{12})$ heteroaryl or a $(C_2\text{-}C_{12})$ heterocycle.

In accordance with one embodiment of the present invention, there is provided a compound of formula (II) or (IV), wherein $R^{6a}$ and $R^{6b}$ together form a (C) heteroaryl.

In accordance with one embodiment of the present invention, there is provided a compound of formula (III) or (IV), wherein $R^1$ is H, X is O and $R^2$ is selected from the group consisting of H, $(C_1\text{-}C_6)$alkyl, —C(O)$R^{10}$, —C(O)N$(R^{6a})(R^{6b})$, —C(O)O$R^{6c}$, —S(O)$_2R^5$, $(C_3\text{-}C_9)$ aryl, $(C_3\text{-}C_{12})$ cycloalkyl, $(C_2\text{-}C_{12})$heterocycle, and $(C_2\text{-}C_{12})$heteroaryl.

In accordance with one embodiment of the present invention, there is provided a compound of formula (III) or (IV), wherein $R^3$ is $C_6$ heteroaryl.

In accordance with one embodiment of the present invention, there is provided a compound of formula (III) or (IV), wherein $R_1$ is C(O)$R_4$, X is O and $R_2$ is C(O)$R_{10}$, wherein $R^4$ is N$(R^6)(R^7)$ and $R_{10}$ is $(C_1\text{-}C_6)$ alkyl or $(C_5\text{-}C_{12})$ aryl. More preferably, $R_6$ is $(C_1\text{-}C_6)$ alkyl (e.g., $C_1$ alkyl) and $R_7$ is $(C_5\text{-}C_{12})$aryl (e.g., $C_6$ aryl optionally substituted by halo). A particularly preferred $R_7$ group is:

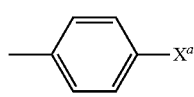

wherein $X^a$ is halo, more preferably e.g., Cl.

Various groups of the formula (I), (II), (III) and (IV) may be optionally substituted with one or more substituents. In terms of non-limiting examples, $R^1$ may be optionally substituted by one or more $R^{11}$; each of $R^2$ and $R^3$ individually or a ring system formed by $R^2$ and $R^3$ together may be optionally substituted by one or more $R^{12}$ or $R^{12a}$ respectively; $R^4$ may be substituted by one or more $R^{15}$; $R^5$ may be substituted by one or more $R^{16}$; $R^6$, $R^{6a}$, $R^{6b}$, $R^{6c}$ and $R^7$ or a ring system formed by any of these groups together may be optionally substituted by one or more $R^{12b}$, $R^{12c}$, $R^{12d}$, $R^{12e}$ and $R^{13}$ respectively; and $R^{10}$ may be substituted by one or more $R^{17}$. In the above embodiments, $R^{11}$, $R^{12}$, $R^{12a}$, $R^{12b}$, $R^{12c}$, $R^{12d}$, $R^{12e}$, $R^{13}$, $R^{15}$, $R^{16}$ and $R^{17}$ are each independently selected from the group consisting of $(C_1\text{-}C_6)$alkyl, $(C_1\text{-}C_6)$alkoxy, halo, oxo, haloalkyl, bihaloalkyl, trihaloalkyl, haloalkoxy, bihaloalkoxy, trihaloalkoxy, hydroxyl, amino, and amide. Particularly preferred substitutions include, without limitation, $C_1$alkyl, oxo, chloro and $CF_3$.

In accordance with one embodiment of the present invention, there is provided a compound having the structure:

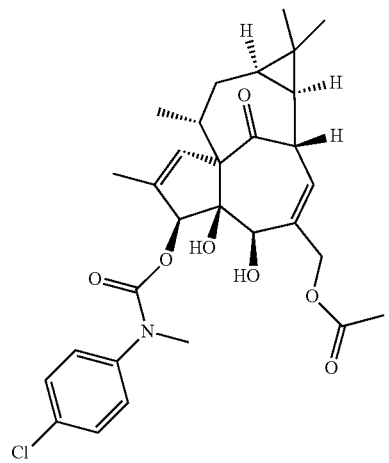

or a pharmaceutically acceptable salt thereof.

In accordance with one embodiment of the present invention, there is provided a compound having the structure:

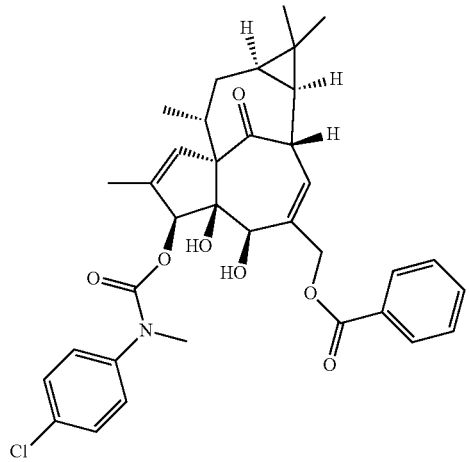 [SMILES: CC1=C[C@]23C(=O)[C@@H](C=C(COC(=O)c4ccccc4)[C@@H](O)[C@]2(O)[C@H]1OC(=O)N(C)c1ccc(Cl)cc1)[C@H]1[C@@H](C[C@H]3C)C1(C)C]

or a pharmaceutically acceptable salt thereof.

In accordance with one embodiment of the present invention, there is provided a compound having the structure:

27

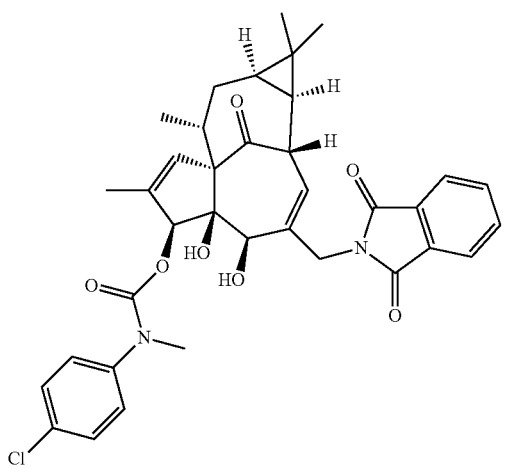 [SMILES: CC1=C[C@]23C(=O)[C@@H](C=C(CN4C(=O)c5ccccc5C4=O)[C@@H](O)[C@]2(O)[C@H]1OC(=O)N(C)c1ccc(Cl)cc1)[C@H]1[C@@H](C[C@H]3C)C1(C)C]

or a pharmaceutically acceptable salt thereof.

In accordance with one embodiment of the present invention, there is provided a compound having the structure:

or a pharmaceutically acceptable salt thereof.

In accordance with one embodiment of the present invention, there is provided a compound having the structure:

or a pharmaceutically acceptable salt thereof.

In accordance with the present invention, there is provided a compound having the structure:

28 or a pharmaceutically acceptable salt thereof.

In accordance with the present invention, there is provided a compound having the structure:

or a pharmaceutically acceptable salt thereof.

In accordance with the present invention, there is provided a compound having the structure:

or a pharmaceutically acceptable salt thereof.

In accordance with the present invention, there is provided a compound having the structure:

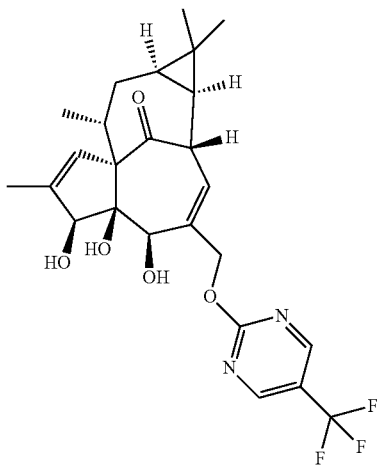 [SMILES: CC1=C[C@]23C(=O)[C@@H](C=C(COc4ncc(C(F)(F)F)cn4)[C@@H](O)[C@]2(O)[C@H]1O)[C@H]1[C@@H](C[C@H]3C)C1(C)C]

or a pharmaceutically acceptable salt thereof.

In accordance with the present invention, there is provided a compound having the structure:

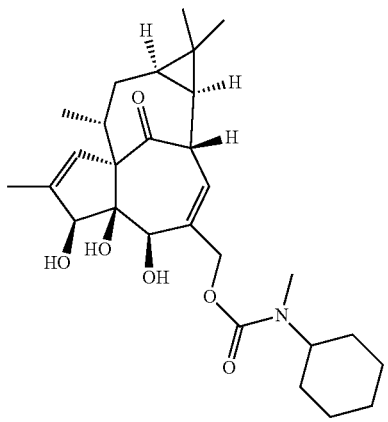 [SMILES: CC1=C[C@]23C(=O)[C@@H](C=C(COC(=O)N(C)C4CCCCC4)[C@@H](O)[C@]2(O)[C@H]1O)[C@H]1[C@@H](C[C@H]3C)C1(C)C]

or a pharmaceutically acceptable salt thereof.

In accordance with the present invention, there is provided a compound having the structure:

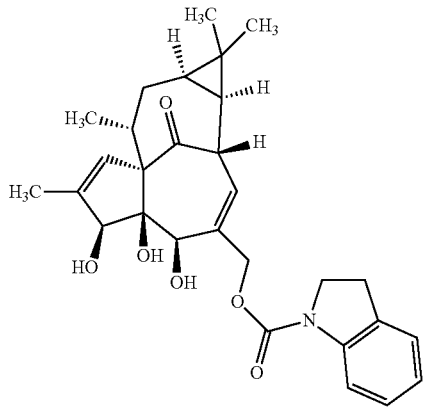 [SMILES: CC1=C[C@]23C(=O)[C@@H](C=C(COC(=O)N4CCc5ccccc54)[C@@H](O)[C@]2(O)[C@H]1O)[C@H]1[C@@H](C[C@H]3C)C1(C)C]

or a pharmaceutically acceptable salt thereof.

In accordance with the present invention, there is provided a compound having the structure:

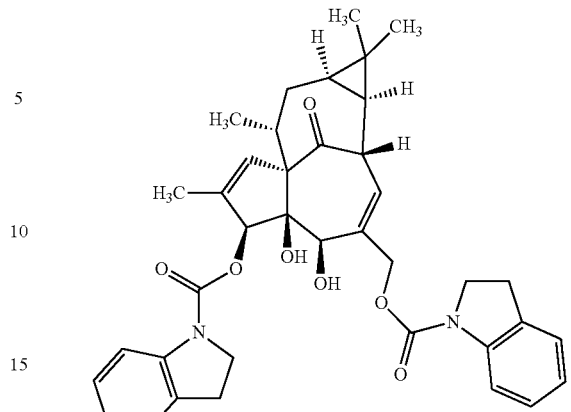

or a pharmaceutically acceptable salt thereof.

In accordance with one embodiment of the present invention, there is provided a pharmaceutical composition comprising a compound of Formula (I), (II), (III) or (IV) in a pharmaceutically acceptable salt thereof, and a pharmaceutically acceptable excipient. In a further embodiment, the compound is present in amorphous form. In a further embodiment, the pharmaceutical composition is in a tablet form. In a further embodiment, the compound is present as a spray dried dispersion.

In accordance with one embodiment of the present invention, there is provided a method of curing an HIV infection in a subject comprising administering to the subject a compound of Formula (I), (II), (III) or (IV), or a pharmaceutically acceptable salt thereof.

In accordance with one embodiment of the present invention, there is provided a method of curing an HIV infection in a subject comprising administering to the subject a pharmaceutical composition as described herein.

In accordance with one embodiment of the present invention, there is provided a method of treating an HIV infection in a subject comprising administering to the subject a compound of Formula (I), (II), (III) or (IV) or a pharmaceutically acceptable salt thereof.

In accordance with one embodiment of the present invention, there is provided a method of treating an HIV infection in a subject comprising administering to the subject a pharmaceutical composition as described herein.

In accordance with one embodiment of the present invention, there is provided a method of preventing an HIV infection in a subject at risk for developing an HIV infection, comprising administering to the subject a compound of Formula (I), (II), (III) or (IV) or a pharmaceutically acceptable salt thereof.

In accordance with one embodiment of the present invention, there is provided a method of preventing an HIV infection in a subject at risk for developing an HIV infection, comprising administering to the subject a pharmaceutical composition as described herein. Furthermore, the compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula (I), (II), (III) or (IV), wherein the compound or salt of the compound is used in the manufacture of a medicament for use in the treatment of an HIV infection in a human.

In another embodiment of the invention, there is provided a compound of Formula (I), (II), (III) or (IV), wherein the compound or salt of the compound is used in the manufacture of a medicament for use in the prevention of an HIV infection in a human.

In another embodiment of the invention, there is provided a compound of Formula (I), (II), (III) or (IV), wherein the compound or salt of the compound is used in the manufacture of a medicament for use in the cure of an HIV infection in a human.

In one embodiment, the pharmaceutical formulation containing a compound of Formula (I), (II) (III) or (IV) or a salt thereof is a formulation adapted for parenteral administration. In another embodiment, the formulation is a long-acting parenteral formulation. In a further embodiment, the formulation is a nano-particle formulation.

The compounds of the present invention and their salts, solvates, or other pharmaceutically acceptable derivatives thereof, may be employed alone or in combination with other therapeutic agents. Therefore, in other embodiments, the methods of treating and/or preventing an HIV infection in a subject may in addition to administration of a compound of Formula (I), (II), (III) or (IV) further comprise administration of one or more additional pharmaceutical agents active against HIV.

In such embodiments, the one or more additional agents active against HIV is selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, dolutegravir, cabotegravir, vicriviroc (Sch-C), Sch-D, TAK779, maraviroc, TAK449, didanosine, tenofovir, lopinavir, and darunavir.

As such, the compounds of the present invention of Formula (I), (II), (III) or (IV) and any other pharmaceutically active agent(s) may be administered together or separately and, when administered separately, administration may occur simultaneously or sequentially, in any order. The amounts of the compounds of Formula (I), (II), (III) or (IV) of the present invention and the other pharmaceutically active agent(s) and the relative timings of administration will be selected in order to achieve the desired combined therapeutic effect.

The administration in combination of a compound of the present invention of Formula (I), (II) (III) or (IV) and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formula (I), (II), (III) or (IV) or salts thereof and the other pharmaceutically active agent(s) and the relative timings of administration will be selected in order to achieve the desired combined therapeutic effect.

In addition, the compounds of the present invention of Formula (I), (II), (III) or (IV) may be used in combination with one or more other agents that may be useful in the prevention, treatment or cure of HIV. Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, dolutegravir, cabotegravir, bictegravir and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

Further examples where the compounds of the present invention may be used in combination with one or more agents useful in the prevention or treatment of HIV are found in Table 1.

TABLE 1

| FDA Approval | Brand Name | Generic Name | Manufacturer |
|---|---|---|---|
| Nucleoside Reverse Transcriptase Inhibitors (NRTIs) | | | |
| 1987 | Retrovir | zidovudine, azidothymidine, AZT, ZDV | GlaxoSmithKline |
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | Etravirine | Tibotec Therapeutics |
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfinavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir + ritonavir, LPV/RTV | Abbott Laboratories |
| 2003 | Reyataz | atazanavir sulfate, ATV | Bristol-Myers Squibb |
| 2003 | Lexiva | fosamprenavir calcium, FOS-APV | GlaxoSmithKline |
| 2005 | Aptivus | tripranavir, TPV | Boehringer Ingelheim |
| 2006 | Prezista | Darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | Maraviroc | Pfizer |
| Integrase Inhibitors | | | |
| 2007 | Isentress | Raltegravir | Merck |
| 2013 | Tivicay | Dolutegravir | ViiV Healthcare |
| — | — | Cabotegravir | |

The scope of combinations of compounds of this invention with HIV agents is not limited to those mentioned above, but includes in principle any combination with any pharmaceutical composition useful for the cure, treatment and/or prevention of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452. Ritonavir is 10-hydroxy-2-methyl-5-(1-methylethyl)-1-1 [2-(1-methylethyl) -4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Ill., as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer. SPI-452 is a compound being developed by Sequoia Pharmaceuticals of Gaithersburg, Md., as a pharmacological enhancer.

In one embodiment of the present invention, a compound of Formula (I), (II), (III) or (IV) is used in combination with ritonavir. In one embodiment, the combination is an oral fixed dose combination. In another embodiment, the compound of Formula (I), (II), (III) or (IV) is formulated as a long acting parenteral injection and ritonavir is formulated as an oral composition. In one embodiment, a kit containing the compound of Formula (I), (II), (III) or (IV) is formulated as a long acting parenteral injection and ritonavir formulated as an oral composition. In another embodiment, the compound of Formula (I), (II), (III) or (IV) is formulated as a long acting parenteral injection and ritonavir is formulated as an injectable composition. In one embodiment, a kit containing the compound of Formula (I), (II), (III) or (IV) is formulated as a long acting parenteral injection and ritonavir formulated as an injectable composition.

In another embodiment of the present invention, a compound of Formula (I), (II), (III) or (IV) is used in combination with GS-9350. In one embodiment, the combination is an oral fixed dose combination. In another embodiment, the compound of Formula (I), (II), (III) or (IV) is formulated as a long acting parenteral injection and GS-9350 is formulated as an oral composition. In one embodiment, there is provided a kit containing the compound of Formula (I), (II), (III) or (IV) formulated as a long acting parenteral injection and GS-9350 formulated as an oral composition. In another embodiment, the compound of Formula (I), (II), (III) or (IV) is formulated as a long acting parenteral injection and GS-9350 is formulated as an injectable composition. In one embodiment, is a kit containing the compound of Formula (I), (II), (III) or (IV) is formulated as a long acting parenteral injection and GS-9350 formulated as an injectable composition.

In one embodiment of the present invention, a compound of Formula (I), (II), (III) or (IV) is used in combination with SPI-452. In one embodiment, the combination is an oral fixed dose combination. In another embodiment, the compound of Formula (I), (II), (III) or (IV) is formulated as a long acting parenteral injection and SPI-452 is formulated as an oral composition. In one embodiment, there is provided a kit containing the compound of Formula (I), (II), (III) or (IV) formulated as a long acting parenteral injection and SPI-452 formulated as an oral composition. In another embodiment, the compound of Formula (I), (II), (III) or (IV) is formulated as a long acting parenteral injection and SPI-452 is formulated as an injectable composition. In one embodiment, there is provided a kit containing the compound of Formula (I), (II), (III) or (IV) formulated as a long acting parenteral injection and SPI-452 formulated as an injectable composition.

In one embodiment of the present invention, a compound of Formula (I), (II), (III) or (IV) is used in combination with compounds which are found in previously filed PCT/CN2011/0013021, which is herein incorporated by reference.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV).

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), wherein said virus is an HIV virus. In some embodiments, the HIV virus is the HIV-1 virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV).

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), wherein said virus is an HIV virus. In some embodiments, the HIV virus is the HIV-1 virus.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), further comprising administration of a therapeutically effective amount of one or more agents active against an HIV virus.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II) (III) or (IV), further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV).

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), wherein said virus is an HIV virus. In some embodiments, the HIV virus is the HIV-1 virus.

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), further comprising administration of a therapeutically effective amount of one or more agents active against an HIV virus.

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II), (III) or (IV), further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In various embodiments, the compounds of the present invention of Formula (I), (II) (III), or (IV) or a pharmaceutically acceptable salt thereof, may be used in treating cancer in a subject comprising administering to the subject a compound of the present invention, pharmaceutically acceptable salt thereof. Combinations of compounds, as well as pharmaceutical compositions of all of the above, are encompasses in such methods of treatment. As used in the context of these methods of treatment, the term "treatment" or "treating" in the context of therapeutic methods, refers to alleviating the specified condition, eliminating or reducing the symptoms of the condition, slowing or eliminating the progression, invasion, or metastatic spread of the condition and preventing or delaying the reoccurrence of the condition in a previously afflicted subject. The present invention further provides use of the compounds of the invention, pharmaceutically acceptable salts thereof, as well as pharmaceutical compositions thereof, as well as for the preparation of a medicament for the treatment of cancer in a mammal (e.g., human) in need thereof. Cancers that may be treated include, without limitation, brain (gliomas), breast cancer, inflammatory breast cancer, colorectal cancer, Wilm's tumor, Ewing's sarcoma, Rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia, Mantle cell leukemia, Multiple myeloma, Megakaryoblastic leukemia, multiple myeloma, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

In further embodiments, the compound of the present invention of Formula (I), (II), (III) or (IV), or a pharmaceutically acceptable salt thereof, is selected from the group of compounds set forth in Table 2.

TABLE 2

| Compound No. | Parent Structure | Chemical Name |
|---|---|---|
| 1 | | ((1aR,2S,5R,5aS,6S,8aS,9R,10aR)-6-(((4-chlorophenyl)(methyl)carbamoyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl acetate |
| 2 | | ((1aR,2S,5R,5aS,6S,8aS,9R,10aR)-6-(((4-chlorophenyl)(methyl)carbamoyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl benzoate |

TABLE 2-continued

| Compound No. | Parent Structure | Chemical Name |
|---|---|---|
| 3 | | (1aR,2S,5R,5aS,6S,8aS,9R,10aR)-4-((1,3-dioxoisoindolin-2-yl)methyl)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-6-yl(4-chlorophenyl)(methyl)carbamate |
| 4 | | (1aR,2S,5R,5aS,8aS,9R,10aR)-5,5a-dihydroxy-4-(hydroxymethyl)-1,1,7,9-tetramethyl-1a,2,5,5a,10,10a-hexahydro-1H-2,8a-methanocyclopenta[a]cyclopropa[e][10]annulene-6,11(9H)-dione |
| 5 | | ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl (4-chlorophenyl)(methyl)Carbamate |
| 6 | | ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10] annulen-4-yl)methyl phenylcarbamate |

TABLE 2-continued

| Compound No. | Parent Structure | Chemical Name |
|---|---|---|
| 7 | | ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl butylcarbamate |
| 8 | | ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl benzylcarbamate |
| 9 | | ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl cyclohexyl(methyl)carbamate |
| 10 | | ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl indoline-1-carboxylate |

TABLE 2-continued

| Compound No. | Parent Structure | Chemical Name |
|---|---|---|
| 11 | | (1aR,2S,5R,5aS,6S,8aS,9R,10aR)-5,5a-dihydroxy-4-(((indoline-1-carbonyl)oxy)methyl)-1,1,7,9-tetramethyl-11-oxo-1a,2,5,5a,6,9,10,10a-octahydro-1H-2,8a-methanocyclopenta[a]cyclopropa[e][10]annulen-6-yl indoline-1-carboxylate |
| 12 | | (1aR,2S,5R,5aR,6S,8aS,9R,10aR)-5,5a,6-trihydroxy-1,1,7,9-tetramethyl-4-(((5-(trifluoromethyl)pyrimidin-2-yl)oxy)methyl)-1a,2,5,5a,6,9,10,10a-octahydro-1H-2,8a-methanocyclopenta[a]cyclopropa[e][10]annulen-11-one |

The compounds of Table 2 were synthesized according to the Examples described below.

In another embodiment, there is provided a pharmaceutical composition comprising a pharmaceutically acceptable diluent and a therapeutically effective amount of a compound of Formula (I), (II), (III) or (IV) or a pharmaceutically acceptable salt thereof.

In certain embodiments, the compound(s) of the present invention, or a pharmaceutically acceptable salt thereof, is chosen from the compounds set forth in Table 2. The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formula (I), (II), (III) or (IV) may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, 3-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, $Na_2CO_3$, $K_2CO_3$, NaH, and potassium-t-butoxide.

Salts derived from pharmaceutically acceptable organic non-toxic bases include salts of primary, secondary, and tertiary amines, including in part, trimethylamine, diethylamine, N, N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences,* 17th ed., Mack Publishing Company, Easton, Pa., 1985, p. 1418, the disclosure of which is hereby incorporated by reference only with regards to the lists of suitable salts.

The compounds of Formula (I), (II), (III) or (IV) of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formula (I), (II), (III) or (IV) containing one or more asymmetric carbon atoms can exist as two or more stereoisomers. Where a compound of Formula (I), (II), (III) or (IV) contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of Formula (I), (II), (III) or (IV), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I or Formula II contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formula (I), (II), (III) or (IV) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula (I), (II), (III) or (IV), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Isotopically-labelled compounds of Formula (I), (II), (III) or (IV) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be administered as prodrugs. Thus, certain derivatives of compounds of Formula (I), (II), (III) or (IV), which may have little or no pharmacological activity themselves can, when administered into or onto the body, be converted into compounds of Formula (I), (II), (III) or (IV) as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see Remington's Pharmaceutical Sciences, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 1-1000 mgmg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

In various embodiments, pharmaceutical compositions of the present invention encompass compounds of Formula (I), (II), (III) or (IV), salts thereof, and combinations of the above.

Compounds of Formulas (I), (II), (III) and (IV) may for example be synthesized according to Schemes 1, 2, 3, 4, 5, 6, 7 or 8 using materials described therein.

In one embodiment, ingenol derivatives of formula 1.1 and 1.2 (Scheme 1) may be prepared by esterification (Esterification, Methods, Reactions, and Applications, $2^{nd}$ edition, Junzo Otera and Joji Nichikido, Wiley-VCH, 2010 and references cited therein; Protecting Groups in Organic Synthesis, $3^{rd}$ edition, Theodora W. Greene, Peter G. M. Wuts, Wiley-Interscience, 1999, pp 149-154.) of ingenol using methods known in the art. For example, compounds of formula 1.1 and 1.2 can be synthesized by reacting ingenol with activated acid derivatives such as acyl halides, acyl thiazolidone, mixed or symmetrical anhydrides or the likes with the presence of a base such as triethylamine, di-isopropylethylamine, pyridine, or 4-(N,N-dimethylamino) pyridine (DMAP) and in suitable solvents such as dichloromethane, or N,N-dimethylformamide, acetonitrile or the like. Esterification with anhydrides can also be carried out in the presence of catalyst such as sulfuric acid, perchloric acid or the like or with Lewis acid such as scandium (III) triflate or the like. Esterification of ingenol with acids can be carried out under the Fischer-Speier condition in the presence of an acid such as p-toluenesulfonic acid, sulfuric acid or the like or a Lewis acid. Alternatively, reaction of acid and ingenol can occur using coupling reagents such as carbodiimides, for example dicyclohexylcarbodiimide (DCC), N,N-di-isopropylcarbodiimide (DIC) or the like in the absence or presence of a base such as DMAP in solvents such as dichloromethane, THF or the like. Esterification can also be carried out using enzymatic conditions such as the use of lipase or esterase with vinyl acetate, propenyl acetate or the like (Neena N. Gandhi et al, Catalysis Reviews, 2000, 42:4, 439-480 and references cited therein).

In another embodiment, ingenol derivatives of formula 1.1 and 1.2 (Scheme 1) representing a class of mono- and bis-carbamates may be prepared by methods for carbamoylation of hydroxy groups (Comprehensive Organic Transformations, $2^{nd}$ Ed, Richard C. Larock, Wiley-VCH, 1999). For example, compounds of formula 1.1 and 1.2 having mono- and di-substituted N-mono-substituted carbamates can be prepared by reacting ingenol with an isocyanate in the absence or presence of base such as triethylamine, di-isopropylethylamine, pyridine, potassium carbonate or the like and in solvents such as dichloromethane, tetrahydrofuran, acetonitrile or N,N-dimethylformamide. Compounds of formula 1.1 and 1.2 having mono- and di-substituted N-di-substituted carbamates can be prepared by reacting ingenol with carbamoyl halides such as carbamoyl chlorides in absence or presence of base such as triethylamine, di-isopropylethylamine, pyridine, potassium carbonate or the like and in solvents such as dichloromethane, tetrahydrofuran, acetonitrile or N,N-dimethylformamide. Isocyanates and carbamoyl halides are either commercially available or can be readily prepared by treatment of corresponding amines with triphosgene, bases such as triethylamine, di-isopropylethylamine and in solvents such as dichloromethane at −20° C. to RT.

Scheme 1

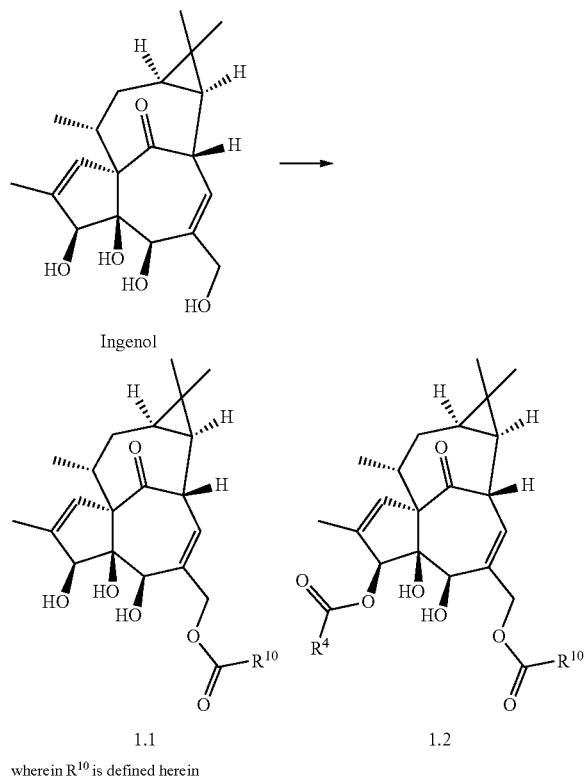

1.1   1.2 wherein R¹⁰ is defined herein

In another embodiment, ingenol derivatives of formula 2.1 and 2.2 (Scheme 2) representing a class of mono- and di-substituted O-heteroaryl compounds may be prepared by treating ingenol with 2-halo-heteroaromatic compounds such as 2-fluoro-heteroaromatic, or 2-chloro-heteroaromatic compounds in the presence of a base such as potassium carbonate, sodium carbonate or the like, potassium tert-butoxide, sodium hydride, cesium fluoride or the like and in solvents such as DMSO, THF, DMF or the like. Alternatively, this reaction can be catalyzed under metal mediated cross coupling conditions such as the use of copper or palladium based salts or ligands. (Niranjan Panda, Ashis K. Jena, Organic Chem., Curr. Res., 2015, 4:130 and references cited therein; Andrei V. Vorogushin, et al, J. Am. Chem. Soc., 2005, 127, 8146-8149 and ref cited therein)

Scheme 2

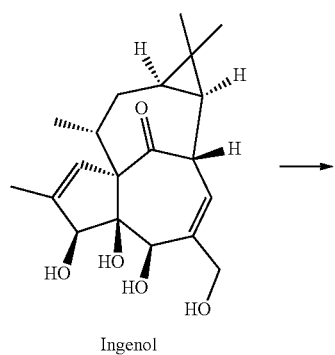

Ingenol

-continued

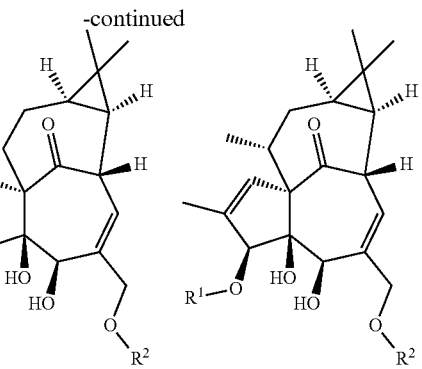

2.1   2.2 wherein R¹ and R² are defined herein

Compounds with formula 3.4, 3.5, 3.6 may be prepared as shown in Scheme 3 using common intermediate 3.3. For example, compound of formula 3.3 with N-carbamate group can be prepared from ingenol through protection of hydroxy groups at 5 and 20 positions through isopropylidene, cyclopentylidene, cyclohexylidene, benzylidene using reagents such as acetone, 2,2-dimethoxypropane, cyclopentanone, cyclohexanone, or benzyladehyde in the presence of an acid catalyst such as p-toluenesulfonic acid, camphorsulfonic acid or the like and in solvents such as dichloromethane, THF, N,N-dimethylformamide, toluene or the like and at RT or heating for azetropic removal of water to give compounds of formula 3.1. Compounds of formula 3.2 with N-mono-substituted carbamates can be prepared by reacting 3.1 with an isocyanate in the absence or presence of base such as triethylamine, di-isopropylethylamine, pyridine, potassium carbonate or the like and in solvents such as dichloromethane, tetrahydrofuran, acetonitrile or N,N-dimethylformamide. Compounds of formula 3.2 having N-di-substituted carbamates can be prepared by reacting ingenol with carbamoyl halides such as carbamoyl chlorides in absence or presence of base such as triethylamine, di-isopropylethylamine, pyridine, potassium carbonate or the like and in solvents such as dichloromethane, tetrahydrofuran, acetonitrile or N,N-dimethylformamide. Protecting groups (PG) in compounds of formula 3.2 can be removed under acidic conditions such as hydrochloric acid, perchloric acid, trifluoroacetic acid, acetic acid or the like and in solvents such as tetrahydrofuran, 1,4-dioxane, methanol or the like to give common intermediate of formula 3.3. In one embodiment, compound of formula 3.3 can be esterified using reaction conditions described above for compounds of formula 1.1 and 1.2 to give compounds of formula 3.4. In another embodiment, compound of formula 3.3 can be carbamoylated using reaction conditions described above for compounds of formula 1.1 and 1.2 to give compounds of formula 3.4. In another embodiment, compound of formula 3.3 can form O-heteroaromatic compounds using reaction conditions described above for compounds of formula 2.1 and 2.2 to give compounds of formula 3.5. In another embodiment, compounds of formula 3.3 can be treated under Mitsunobu conditions such as triphenyl phosphine, diethyl azodicarboxylate (DEAD), diisopropyl azodicarboxylate (DIAD) and phthalimide or the like to give compounds of formula 3.6 (Oyo Mitsunobu, Synthesis, 1981, 1-28 and references cited therein).

Scheme 3

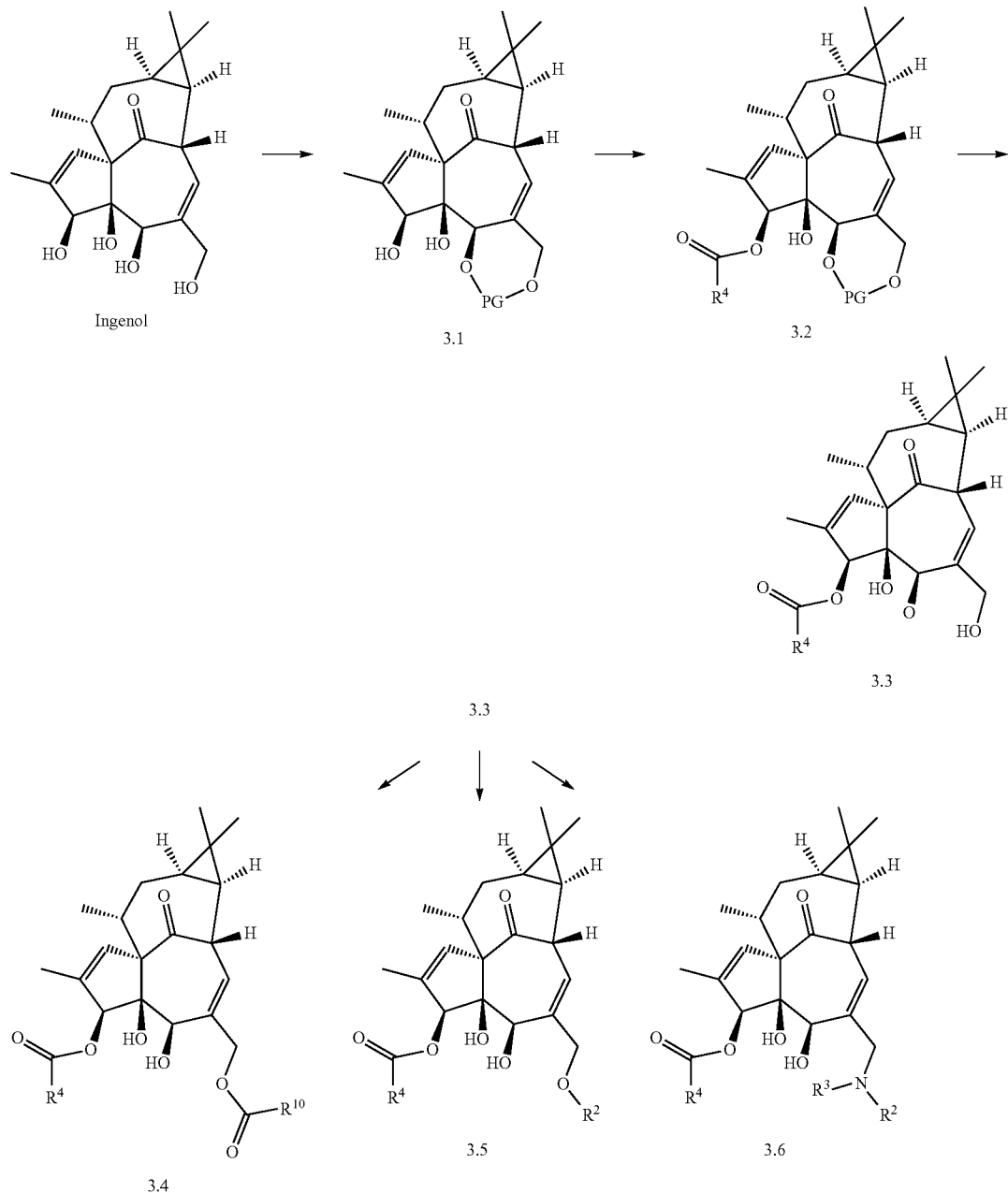

wherein $R^2$, $R^3$, $R^4$ and $R^{10}$ are defined herein

Compounds of formula 4.4 may be prepared from ingenol as shown in Scheme 4. For example, protection of ingenol using silicon protecting groups with reagents such as tert-butyldimethylsilyl chloride, chlorodimethyl(iso-propyl)silane, chlorodiethyl(iso-propyl)silane or the like in the presence of a base such as imidazole, triethylamine, di-isopropylethylamine or the like in solvents such as dichloromethane, N,N-dimethylformamide or the like can prepare compounds of formula 4.1. Compounds of formula 4.1 can be treated with triethylamine trihydrofluoride or the like at −20° C.-10° C. to prepare compounds of formula 4.2. Compounds of formula 4.3 with N-mono-substituted carbamates can be prepared by reacting 4.2 with an isocyanate in the absence or presence of base such as triethylamine, di-isopropylethylamine, pyridine, potassium carbonate or the like and in solvents such as dichloromethane, tetrahydrofuran, acetonitrile or N,N-dimethylformamide. Compounds of formula 3.2 having N-di-substituted carbamates can be prepared by reacting ingenol with carbamoyl halides such as carbamoyl chlorides in absence or presence of base such as lithium bis(trimethylsilyl)amide, di-isopropylethylamine, pyridine, potassium carbonate or the like and in solvents such as dichloromethane, tetrahydrofuran, acetonitrile or N,N-dimethylformamide. Compounds of formula 4.4 can be prepared by treatment of 4.3 with acids such as hydrochloric acid, trifluoroacetic acid or the like in solvents such as tetrahydrofuran, 1,4-dioxane, methanol or the like. Alternatively, fluoride reagents such tetra-butylammonium fluoride, triethylamine trihydrofluoride, or the like in solvents such as tetrahydrofuran can be used for the removal of silyl protecting group in 4.3.

Scheme 4

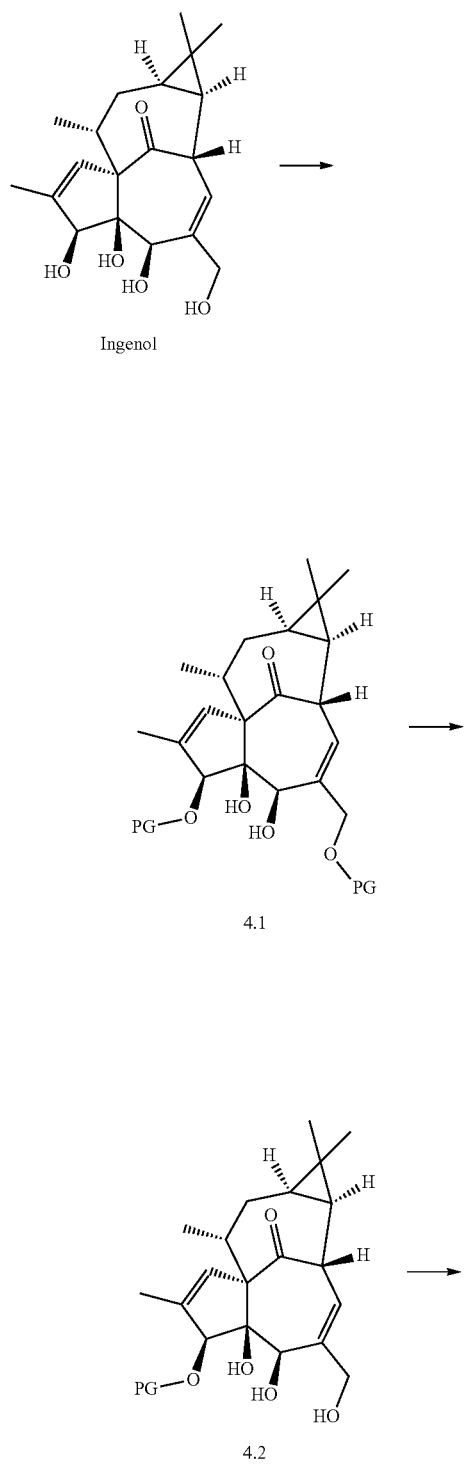

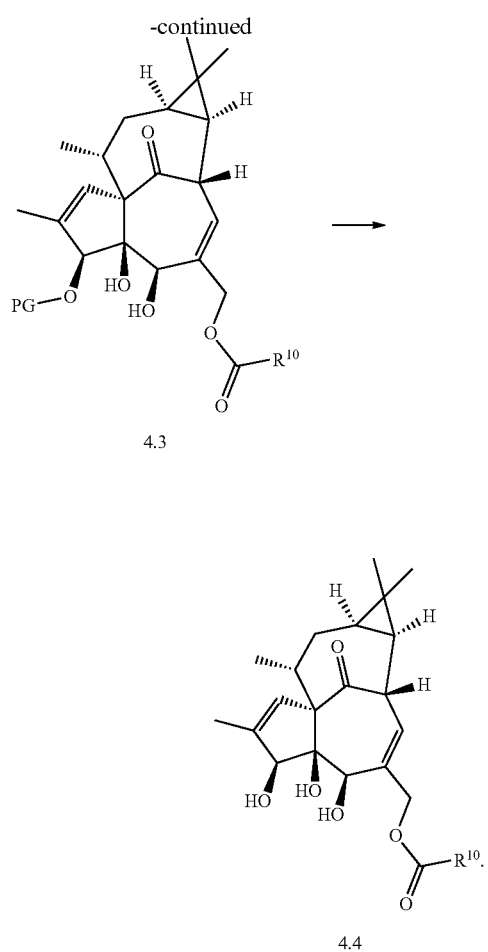

wherein $R^{10}$ is defined herein

Compounds of formula 5.2, 5.3, 5.4, 5.4 may be prepared as shown in Scheme 5. Compounds of formula 5.1 can be synthesized by oxidation of compounds of formula 3.1 (see Scheme 3) by reagents such as pyridinium chlorochromate (PCC), pyridinium dichromate (PDC), Dess-Martin periodinane (DMP), 2-iodoxybenzoic acid, DMSO/oxalyl chloride, or the like in solvents such as dichloromethane. Compound of formula 5.2 can be prepared by removal of protecting group (PG) in compounds of formula 5.1 under acidic conditions such as hydrochloric acid, perchloric acid, trifluoroacetic acid, acetic acid or the like and in solvents such as tetrahydrofuran, 1,4-dioxane, methanol or the like. In one embodiment, compound of formula 5.2 can be esterified using reaction conditions described above for compounds of formula 1.1 and 1.2 to give compounds of formula 5.3. In another embodiment, compound of formula 5.2 can be carbamoylated using reaction conditions described above for compounds of formula 1.1 and 1.2 to give compounds of formula 5.3. In another embodiment, compound of formula 5.2 can form O-heteroaromatic compounds using reaction conditions described above for compounds of formula 2.1 and 2.2 to give compounds of formula 5.4. In another embodiment, compounds of formula 5.2 can be treated under Mitsunobu conditions such as triphenyl phosphine, diethyl azodicarboxylate (DEAD), diisopropyl azodicarboxylate (DIAD) and phthalimide or the like to give compounds of formula 5.5.

Scheme 5
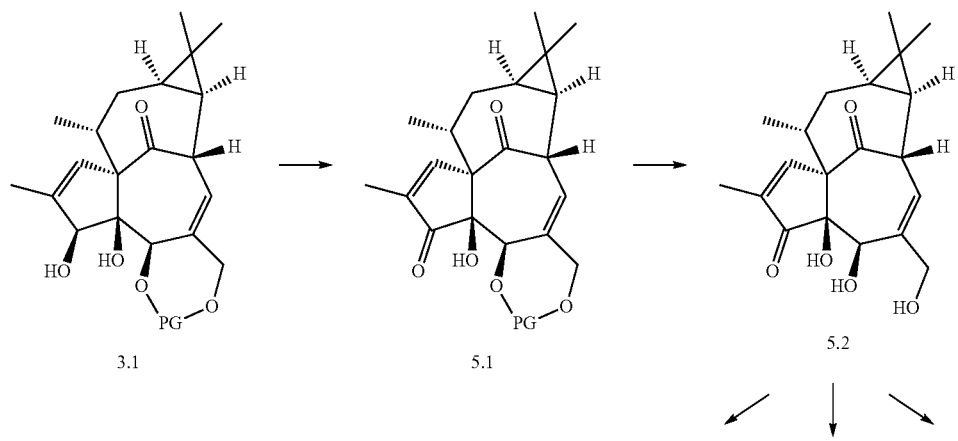
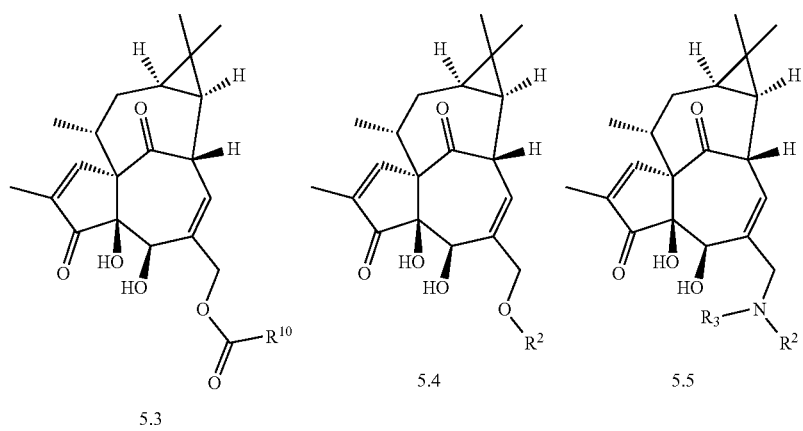
wherein R², R³, and R¹⁰ are defined herein

Compound of formula 6.1 represents an array of ingenol diastereoisomers. Examples of ingenol diastereosiomers are depicted in Scheme 6 such as compounds of formula 6.2-6.10 but not limited to the list. Total synthesis of racemic and chiral ingenols have been reported in the literature (J. D. Winkler, et. al. J. Am. Chem. Soc. 2002, 124, 9726; K. Tanino, et. al. J. Am. Chem. Soc. 2003, 125, 1498; J. L. Wood et. al. J. Am. Chem. Soc. 2004, 126, 16300; S. J. McKerrall et al, J. Am. Chem. Soc., 2014, 136, 5799). For example, the use of chiral columns can result in the separation of enantiomers of ingenols. Alternatively, the use of enantiomeric starting materials as those reported in the literature can result enantiomeric ingenols.

Scheme 6

6.1

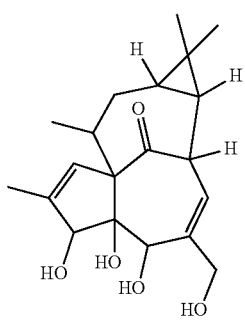

Examples:

Ingenol 6.2

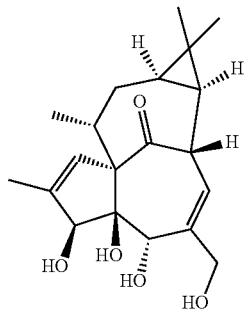

6.3

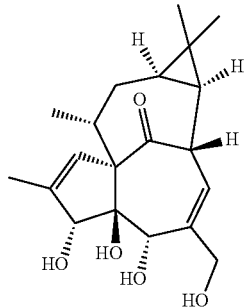

6.4

6.5

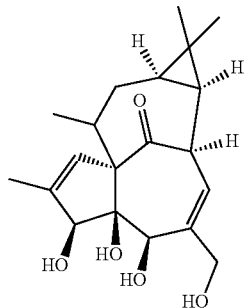

6.6

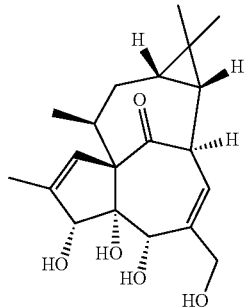

enant-Ingenol 6.7

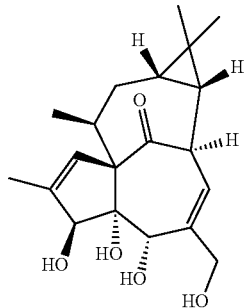

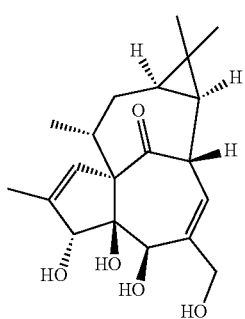

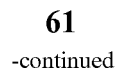
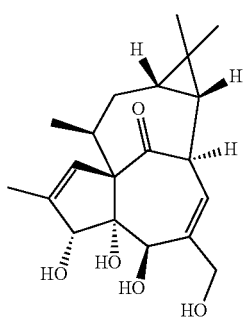

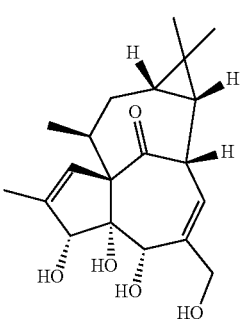

For example, ingenol diastereoisomers of formula 6.2 and 6.3 may be prepared in Scheme 7. The use of an oxidation/chiral reduction strategy of protected ingenol such as compound of formula 5.1 can give compound of formula 7.1 which upon removal of protecting group can give compound of formula 6.2. Reducing agents such as boranes or catecholboranes with chiral oxaborolidene catalyst, rhodium (I) and rhodium (III) salts with PYBOX ligands or the like can achieve this transformation (E. J. Corey, R. K. Balzski, Tetrahedron Lett. 1990, 31, 611; H. Nishiyama, et al, Organometallics 1991, 10, 500). In another example, ketone of formula 7.2 can be prepared by oxidation of protected ingenol of formula 4.1 using reagents such as pyridinium chlorochromate (PCC), pyridinium dichromate (PDC), Dess-Martin periodinane (DMP), 2-iodoxybenzoic acid, DMSO/oxalyl chloride, or the like in solvents such as dichloromethane. Reduction of compound of formula 7.2 such reagents described above can provide compound of formula 7.3 which upon removal of protecting groups can give ingenol derivative of formula 6.3. Alternatively, this transformation can be carried out by the incorporation of leaving group such as mesylate, triflate, or halide or the like to give compound of formula 7.4. This can be carried out using mesyl chloride, triflic anhydride or the like to give compound of formula 7.4. Compound of formula 7.4 can be treated with an oxygen nucleophile such as potassium hydroxide, sodium benzoate (followed by hydrolzsis) or the like to provide a compound of formula 7.3 with inversion of stereochemistry. Compound of formula of 6.3 can be prepared by removal of protecting groups in 7.3 using methods described previously.

Scheme 7

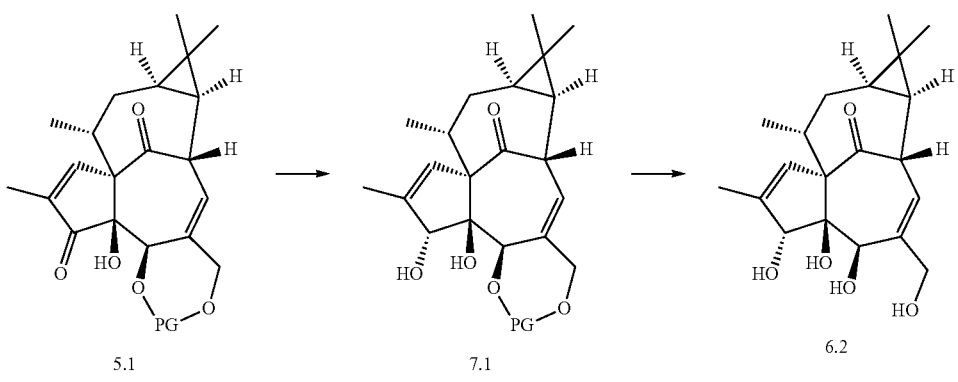

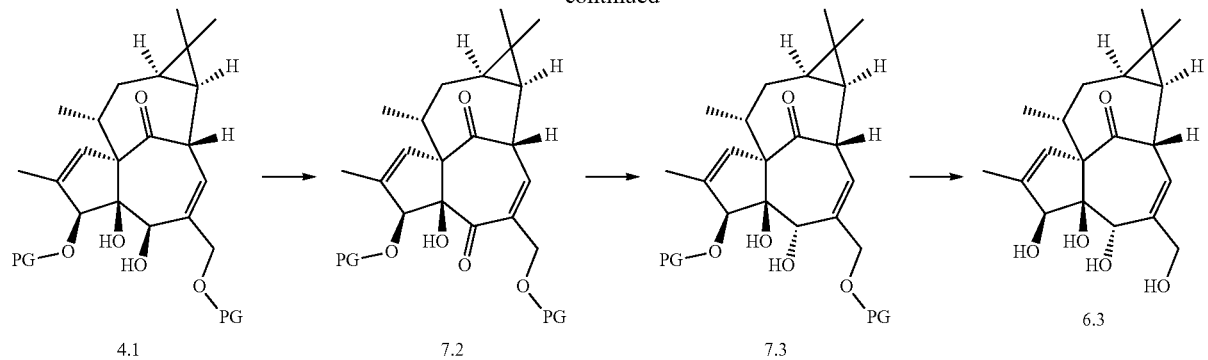
As shown in Scheme 8, compounds of formula 8.1-8.9 may be prepared from compounds of formula 6.1 using similar methods as described in Schemes 1-7.
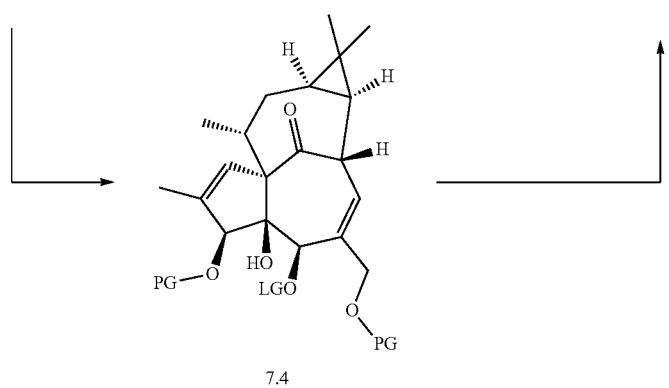
Scheme 8
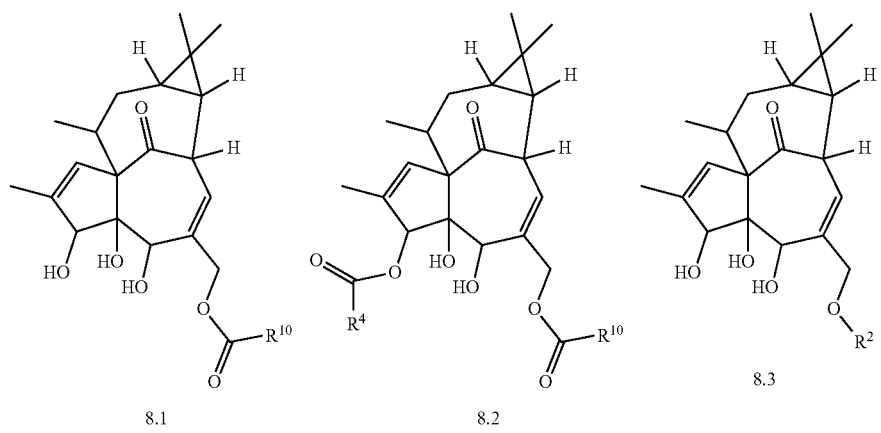

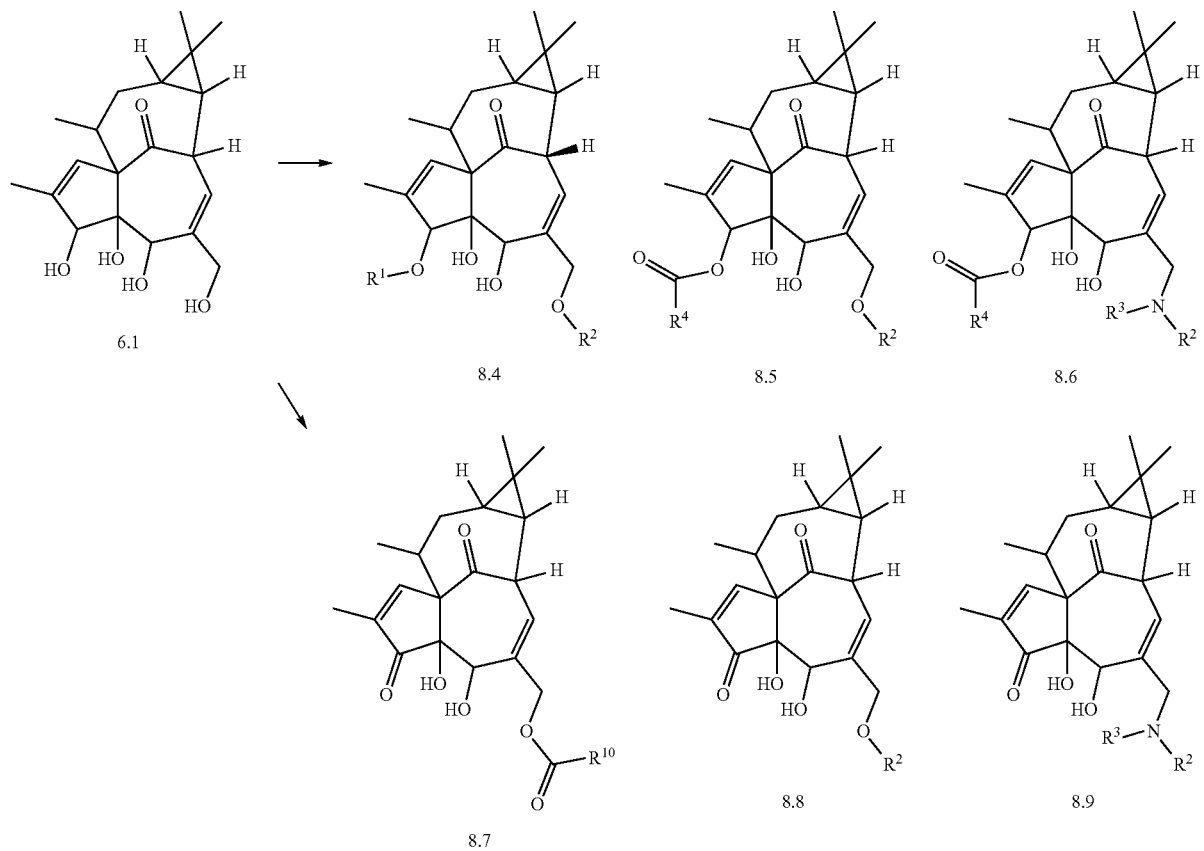

wherein R², R³, R⁴ and R¹⁰ are defined herein

Synthetic Methods

Further to the above, the methods of synthesis for the provided chemical entities may employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein. Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=Aqueous
μL=Microliters
μM=Micromolar
NMR=nuclear magnetic resonance
Boc=tert-butoxycarbonyl
Br=Broad
Cbz=Benzyloxycarbonyl
D=Doublet
Δ=chemical shift
° C.=degrees celcius
DCM=Dichloromethane
Dd=doublet of doublets
DMEM=Dulbeco's Modified Eagle's Medium
DMF=N,N-dimethylformamide
DMSO=Dimethylsulfoxide
EtOAc=ethyl acetate
G=Gram
h or hr=Hours
HCV=hepatitus C virus
HPLC=high performance liquid chromatography
Hz=Hertz
IU=International Units
$IC_{50}$=inhibitory concentration at 50% inhibition
J=coupling constant (given in Hz unless otherwise indicated)
M=Multiplet
M=Molar
$M+H^+$=parent mass spectrum peak plus $H^+$
Mg=Milligram
Min=Minutes
mL=Milliliter
mM=Millimolar
Mmol=Millimole
MS=mass spectrum
Nm=Nanomolar
Ppm=parts per million
q.s.=sufficient amount
S=Singlet
RT=room temperature
sat.=Saturated
T=Triplet
TFA=trifluoroacetic acid Equipment Description $^1$H NMR spectra were recorded on a Varian spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters (Acquity). The following conditions were employed described below.
MS Conditions:
Instrument: Waters SQD
Serial Number: F06SQD018N
Scan Mode: Alternating Positive/Negative Electrospray
Scan Range: 125-1200 amu
Scan Time: 150 msec
Interscan Delay: 50 msec
LC Conditions:
The UPLC analysis was conducted on a Phenomenex Kinetex 1.7 um
2.1×50 mm XB-C18 column at 40° C.
0.2 uL of sample was injected using PLNO (partial loop with needle overfill) injection mode.
The gradient employed was:
Mobile Phase A: Water+0.2% v/v Formic Acid
Mobile Phase B: Acetonitrile+0.15% v/v Formic Acid

| Time | % A | % B | Flow Rate |
| --- | --- | --- | --- |
| 0.00 min | 95 | 5 | 1 ml/min |
| 1.1 min | 1 | 99 | 1 ml/min |
| 1.5 min | 1 | 99 | 1 ml/min |

UV detection provided by summed absorbance signal from 210 to 350 nm scanning at 40 Hz.

Schemes and Experimental Procedures

The following schemes and procedures illustrate how compounds of the present invention can be prepared. The specific solvents and reaction conditions referred to are also illustrative and are not intended to be limiting. Compounds not described are either commercially available or are readily prepared by one skilled in the art using available starting materials. The Examples disclosed herein are for illustrative purposes only and are not intended to limit the scope of the invention.

This in no way is meant to limit the scope of the invention or utility of the compounds of Formulas (I), (II), (III) or (IV). Additional examples contained within were determined to have the shown configuration by spectroscopic methods well known to those skilled in the art including, but not limited to, 1D and 2D NMR methods, vibrational circular dichroism and X-ray crystallography.

Example 1

((1aR,2S,5R,5aS,6S,8aS,9R,10aR)-6-(((4-chlorophenyl) (methyl)carbamoyl)oxy)-5,5a-dihydroxy-1,1,7,9-tetramethyl-11-oxo-1a,2,5,5a,6,9,10,10a-octahydro-1H-2,8a-methanocyclopenta[a] cyclopropa[e][10]annulen-4-yl)methyl acetate

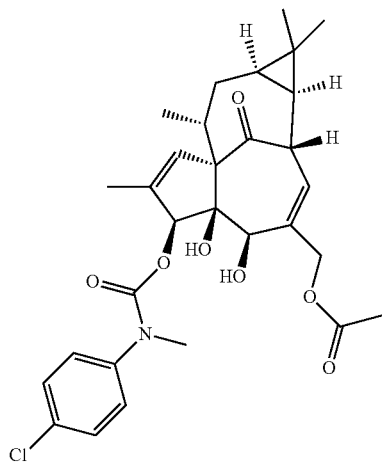 [SMILES: CC(=O)OCC1=C[C@@H]2C(=O)[C@]3(C=C(C)[C@H](OC(=O)N(C)c4ccc(Cl)cc4)[C@@]3(O)[C@@H]1O)[C@H](C)C[C@@H]1[C@H]2C1(C)C]

To a solution of (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e][10]annulen-6-yl (4-chlorophenyl)(methyl)carbamate (50 mg, 0.097 mmol) in dichloromethane (1 mL) at RT was added hunig's base (0.051 mL, 0.291 mmol), acetic anhydride (10.06 μl, 0.107 mmol) and DMAP (0.592 mg, 4.84 μmol). After 1 hour, the solvent was removed under reduced pressure. The crude was purified by C18 column using ISCO instrument [20-80% ACN gradient, 0.1% formic acid, 150 g column] to give ((1aR,2S,5R,5aS,6S,8aS,9R,10aR)-6-(((4-chlorophenyl)(methyl)carbamoyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl acetate (38.2 mg, 0.065 mmol, 67.1% yield) as white solid. $^1$H NMR (400 MHz, CHLOROFORM-d) δ ppm 0.62-0.70 (m, 1H), 0.79 (br. s., 3 H), 0.92 (dd, J=11.4, 8.7 Hz, 1 H), 1.05 (s, 3 H), 1.07 (s, 3 H), 1.60-1.68 (m, 1 H), 1.77 (br. s., 3 H), 2.05 (s, 3 H), 2.07-2.26 (m, 1 H), 3.30 (s, 3 H), 3.48 (br. s., 2 H), 3.82 (d, J=4.9 Hz, 1 H), 4.02 (d, J=8.4 Hz, 1 H), 4.48 (d, J=12.5 Hz, 1 H), 4.72 (d, J=12.5 Hz, 1 H), 5.34 (s, 1 H), 5.94 (br. s., 1 H), 6.09 (d, J=4.2 Hz, 1 H), 7.20 (d, J=7.7 Hz, 2 H), 7.34 (d, J=8.6 Hz, 2 H); LCMS(ESI) m/z: 558.6 (M+1).

Example 2

((1aR,2S,5R,5aS,6S,8aS,9R,10aR)-6-(((4-chlorophenyl) (methyl)carbamoyl)oxy)-5,5a-dihydroxy-1,1,7,9-tetramethyl-11-oxo-1a,2,5,5a,6,9,10,10a-octahydro-1H-2,8a-methanocyclopenta [a]cyclopropa[e][10]annulen-4-yl)methyl benzoate

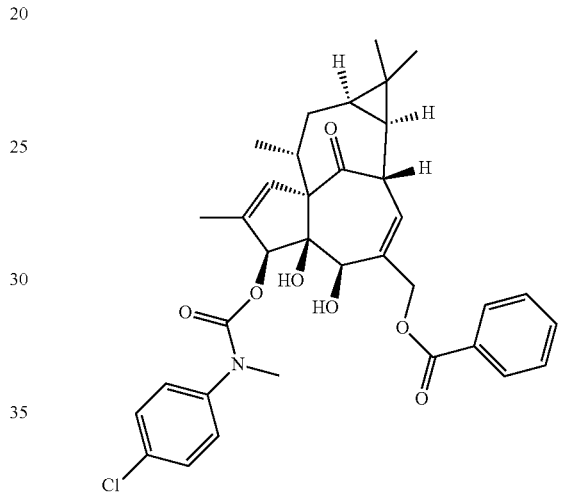

To a solution of (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e][10]annulen-6-yl (4-chlorophenyl)(methyl)carbamate (50 mg, 0.097 mmol) in dichloromethane (1 mL) at RT was added hunig's base (0.051 mL, 0.291 mmol), benzoic anhydride (24.11 mg, 0.107 mmol) and DMAP (0.592 mg, 4.84 μmol). After 5 hours, the mixture was loaded on silica gel column (24 g ISCO column) and eluted with 50-100% (30% EtOAc in hexanes) in hexanes to give ((1aR,2S,5R,5aS,6S,8aS,9R,10aR)-6-(((4-chlorophenyl)(methyl)carbamoyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl benzoate (47.7 mg, 0.076 mmol, 79% yield) as white solid. $^1$H NMR (400 MHz, CHLOROFORM-d) δ ppm 0.62-0.70 (m, 1H), 0.72-0.87 (m, 3 H), 0.94 (dd, J=11.4, 8.6 Hz, 1 H), 1.05 (s, 3 H), 1.08 (s, 3 H), 1.60-1.66 (m, 1 H), 1.76 (br. s., 3 H), 2.09 (br. s., 1 H), 3.30 (s, 3 H), 3.48 (br. s., 1 H), 3.62 (br. s., 1 H), 3.88 (d, J=5.5 Hz, 1 H), 4.06 (d, J=9.0 Hz, 1 H), 4.75 (d, J=12.8 Hz, 1 H), 4.99 (d, J=12.8 Hz, 1 H), 5.36 (s, 1 H), 5.95 (br. s., 1 H), 6.19 (d, J=4.2 Hz, 1 H), 7.21 (d, J=7.9 Hz, 2 H), 7.34 (d, J=8.6 Hz, 2 H), 7.40-7.48 (m, 2 H), 7.53-7.59 (m, 1 H), 8.01 (d, J=7.7 Hz, 2H); LCMS(ESI) m/z: 620.5 (M+1).

Example 3

(1aR,2S,5R,5aS,6S,8aS,9R,10aR)-4-((1,3-diox-oisoindolin-2-yl)methyl)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-6-yl (4-chlorophenyl) (methyl)carbamate

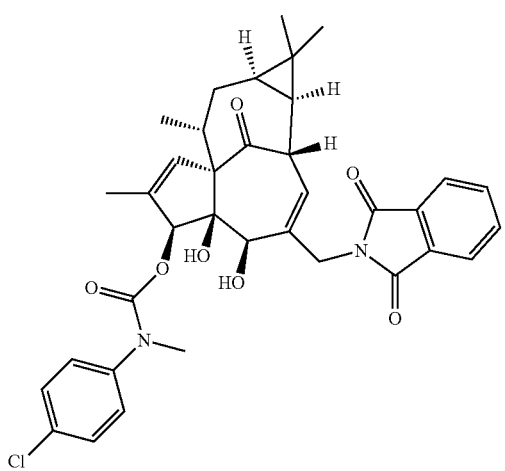 [SMILES: CC1=C[C@]23C(=O)[C@@H](C=C(CN4C(=O)c5ccccc5C4=O)[C@@H](O)[C@]2(O)[C@H]1OC(=O)N(C)c1ccc(Cl)cc1)[C@H]1[C@@H](C[C@H]3C)C1(C)C]

To a solution of (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e][10]annulen-6-yl (4-chlorophenyl)(methyl)carbamate (57 mg, 0.110 mmol), triphenylphosphine (43.5 mg, 0.166 mmol), phthalimide (24.38 mg, 0.166 mmol) in tetrahydrofuran (1 mL) at RT was added DIAD (0.032 mL, 0.166 mmol). After 45 min, the mixture was purified by silica gel chromatography [5-80% EtOAc in hexanes, 24 g ISCO column] to give the product which was contaminated with triphenylphosphine oxide. This material was further purified by C18 column using ISCO instrument with 30-100% ACN gradient (0.1% formic acid) to give (1aR,2S,5R,5aS,6S,8aS,9R,10aR)-4-((1,3-dioxoisoindolin-2-yl)methyl)-5,5a-dihydroxy-1,1,7,9-tetramethyl-1-oxo-1a,2,5,5a,6,9,10,10a-octahydro-1H-2,8a-methanocyclopenta[a]cyclopropa[e][10]annulen-6-yl (4-chlorophenyl)(methyl)carbamate (47.3 mg, 0.070 mmol, 63.1% yield) as white solid. $^1$H NMR (400 MHz, CHLOROFORM-d) δ ppm 0.57-0.66 (m, 1 H), 0.76 (br. s., 3 H), 0.87 (dd, J=11.6, 8.5 Hz, 1 H), 1.02 (s, 3 H), 1.05 (s, 3 H), 1.60-1.64 (m, 1 H), 1.74 (br. s., 3 H), 2.10 (br. s., 1 H), 3.30 (s, 3 H), 3.50 (br. s, 1 H), 3.78 (d, J=4.6 Hz, 1 H), 4.03 (d, J=8.8 Hz, 1 H), 4.25-4.32 (m, 2 H), 4.33-4.40 (m, 1 H), 5.44 (s, 1 H), 5.89 (br. s., 1 H), 6.06 (d, J=4.2 Hz, 1 H), 7.21 (d, J=8.1 Hz, 2 H), 7.32 (d, J=8.8 Hz, 2 H), 7.69-7.75 (m, 2 H), 7.80-7.86 (m, 2 H); LCMS(ESI) m/z: 645.6 (M+1).

Example 4

Synthesis of (1aR,2S,5R,5aS,8aS,9R,10aR)-5,5a-dihydroxy-4-(hydroxymethyl)-1,1,7,9-tetramethyl-1a,2,5,5a,10,10a-hexahydro-1H-2,8a-methanocyclopenta[a]cyclopropa[e][10]annulene-6,11 (9H)-dione

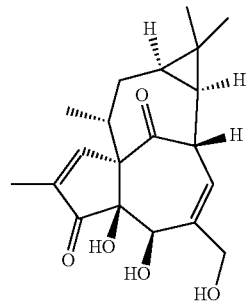 [SMILES: CC1=C[C@]23C(=O)[C@@H](C=C(CO)[C@@H](O)[C@]2(O)C1=O)[C@H]1[C@@H](C[C@H]3C)C1(C)C]

Step 1: (6S,6aR,7aR,9R,9aS,12aS,12bR)-12a-hydroxy-2,2,7,7,9,11-hexamethyl-6,6a,7,7a,8,9,12a,12b-octahydro-6,9a-methanocyclopenta[9,10]cyclopropa[5,6]cyclodeca [1,2-d][1,3]dioxine-12,13(4H)-dione To a suspension of (6S,6aR,7aR,9R,9aS,12S,12aR,12bR)-12,12a-dihydroxy-2,2,7,7,9,11-hexamethyl-4,6,6a,7,7a,8,9,12,12a,12b-decahydro-6,9a-methanocyclopenta[9,10]cyclopropa[5,6]cyclodeca[1,2-d][1,3]dioxin-13-one (133 mg, 0.342 mmol) and 3A molecular sieves (250 mg, 0.342 mmol) in dichloromethane (2 mL) was added PCC (89 mg, 0.411 mmol) in one portion. After 1 day, PCC (37 mg, 0.5 eq) was added. After 1 day, the mixture was filtered through Celite. The crude was absorbed on silica gel and purified by column chromatography [5-60% (30% EtOAc in hexanes) in hexanes, 24 g ISCO column] to give (6S,6aR,7aR,9R,9aS,12aS,12bR)-12a-hydroxy-2,2,7,7,9,11-hexamethyl-6,6a,7,7a,8,9, 12a,12b-octahydro-6,9a-methanocyclopenta[9,10]cyclopropa[5,6]cyclodeca[1,2-d][1,3]dioxine-12,13(4H)-dione (40.3 mg, 0.104 mmol, 30.5% yield) as white solid. $^1$H NMR (400 MHz, CHLOROFORM-d) δ ppm 0.69-0.78 (m, 1 H), 0.93 (d, J=7.1 Hz, 3 H), 0.99 (dd, J=11.9, 8.8 Hz, 1 H), 1.07 (s, 3 H), 1.13 (s, 3 H), 1.16 (s, 3 H), 1.34 (s, 3 H), 1.75-1.91 (m, 5 H), 2.21-2.32 (m, 2 H), 3.69 (s, 1 H), 3.93-4.03 (m, 2 H), 4.10 (d, J=14.7 Hz, 1 H), 4.20 (d, J=14.8 Hz, 1 H), 5.75 (d, J=1.5 Hz, 1 H), 7.51 (s, 1 H); LCMS(ESI) m/z: 385.4 (M+1).

Step 2: (1aR,2S,5R,5aS,8aS,9R,10aR)-5,5a-dihydroxy-4-(hydroxymethyl)-1,1,7,9-tetramethyl-1a,2,5,5a,10,10a-hexahydro-1H-2,8a-methanocyclopenta[a]cyclopropa[e][10]annulene-6,11 (9H)-dione A solution of (6S,6aR,7aR,9R,9aS,12aS,12bR)-12a-hydroxy-2,2,7,7,9,11-hexamethyl-6,6a,7,7a,8,9,12a,12b-octahydro-6,9a-methanocyclopenta[9,10]cyclopropa [5,6]cyclodeca[1,2-d][1,3]dioxine-12,13(4H)-dione (37.8 mg, 0.098 mmol) and 4 N HCl (0.012 mL, 0.049 mmol) was stirred in tetrahydrofuran (1 mL) at RT. After 5 days, the solvent was removed under reduced pressure. The crude was purified by C18 column [5-65% ACN gradient, 0.1% formic acid, 24gISCO C18 column] to give (1aR,2S,5R,5aS,8aS,9R,10aR)-5,5a-dihydroxy-4-(hydroxymethyl)-1,1,7,9-tetramethyl-1a,2,5,5a,10,10a-hexahydro-1H-2,8a-methanocyclopenta[a]cyclopropa[e][10]annulene-6,11 (9H)-dione (22.1 mg, 0.063 mmol, 64.6% yield) as white solid. $^1$H NMR (400 MHz, DMSO-d6) δ ppm 0.66 (q, J=7.6 Hz, 1 H), 0.80-0.88 (m, 4 H), 1.04 (s, 3 H), 1.06 (s, 3 H), 1.63-1.73 (m, 1 H), 1.75 (s, 3 H), 2.09-2.25 (m, 2 H), 3.70 (d, J=9.7 Hz, 1 H), 3.81 (dd, J=14.5, 4.8 Hz, 1 H), 3.90 (dd, J=14.7, 5.3 Hz, 1 H), 4.04 (d, J=11.5 Hz, 1 H), 4.58 (t, J=5.7 Hz, 1 H), 4.93 (d, J=9.7 Hz, 1 H), 5.84-5.89 (m, 1 H), 6.08 (s, 1 H), 7.45 (s, 1 H); LCMS(ESI) m/z: 345.4 (M-1).

Example 5

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl (4-chlorophenyl)(methyl)carbamate

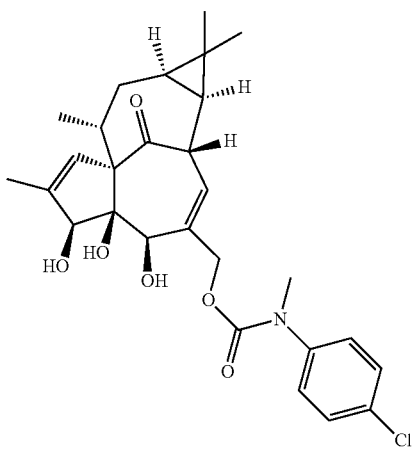 [SMILES: CC1=C[C@]23C(=O)[C@@H](C=C(COC(=O)N(C)c4ccc(Cl)cc4)[C@@H](O)[C@]2(O)[C@H]1O)[C@H]1[C@@H](C[C@H]3C)C1(C)C]

To a solution of ingenol in N,N-Dimethylformamide (1 ml) at 0° C. (ice-water bath) was added (4-chlorophenyl)(methyl)carbamic chloride (35.1 mg, 0.172 mmol). After 15 min, potassium carbonate (59.5 mg, 0.430 mmol) was added. After 15 min, the mixture was allowed to stir at RT. After 2 days, water (2 mL) was added followed by conc. HCl (100 uL). The crude was purified by C18 column [15-100% ACN gradient, 0.1% formic acid, 24gISCO C18 column] to give ((1aR,2S,5R,5aR,6S,8aS,9R,10aR)-5,5a,6-trihydroxy-1,1,7,9-tetramethyl-1-oxo-1a,2,5,5a,6,9,10,10a-octahydro-1H-2,8a-methanocyclopenta[a]cyclopropa[e][10]annulen-4-yl)methyl (4-chlorophenyl)(methyl)carbamate (15.1 mg, 0.029 mmol, 19.98% yield) as white solid. $^1$H NMR (400 MHz, CHLOROFORM-d) δ ppm 0.66-0.74 (m, 1 H), 0.91-0.95 (m, 1 H), 0.97 (d, J=7.0 Hz, 3 H), 1.06 (s, 3 H), 1.10 (s, 3 H), 1.76 (dt, J=15.6, 5.6 Hz, 1 H), 1.84 (s, 3 H), 2.20-2.38 (m, 2 H), 2.63 (br. s., 1 H), 3.26 (s, 3 H), 3.54 (br. s., 1 H), 4.03 (s, 1 H), 4.08 (dd, J=11.4, 3.5 Hz, 1 H), 4.34 (s, 1 H), 4.55 (d, J=12.5 Hz, 1 H), 4.76 (d, J=12.1 Hz, 1 H), 5.92 (s, 1 H), 6.04 (br. d, J=2.6 Hz, 1 H), 7.13 (d, J=8.2 Hz, 2 H), 7.29 (d, J=8.6 Hz, 2 H); LCMS(ESI) m/z: 516.5, 518.4 (M+1).

Example 6

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl phenylcarbamate

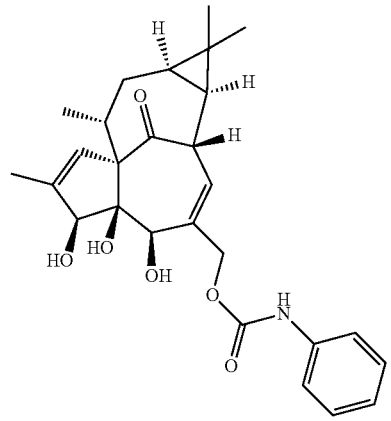 [SMILES: CC1=C[C@]23C(=O)[C@@H](C=C(COC(=O)Nc4ccccc4)[C@@H](O)[C@]2(O)[C@H]1O)[C@H]1[C@@H](C[C@H]3C)C1(C)C]

To a solution of ingenol (100 mg, 0.287 mmol) in dichloromethane (DCM) (2 mL) and N,N-dimethylformamide (DMF) (0.2 mL) at RT was added phenyl isocyanate (0.037 mL, 0.344 mmol). After 5 hours 20 min, the solvent was removed under reduced pressure. The crude was diluted with EtOAc (15 mL) and washed with water (2 mL). The organic phase was collected and concentrated under reduced pressure. The crude was purified by C18 column using an ISCO instrument [5-100% ACN gradient, 0.1% formic acid, 150 g ISCO C18 column] to give ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl phenylcarbamate (62.1 mg, 0.130 mmol, 45.4% yield) as white solid. $^1$H NMR (400 MHz, CHLOROFORM-d) δ ppm 0.68-0.76 (m, 1 H), 0.93-1.00 (m, 4 H), 1.06 (s, 3 H), 1.12 (s, 3 H), 1.77 (dt, J=15.5, 5.6 Hz, 1 H), 1.84 (s, 3 H), 2.22-2.41 (m, 2 H), 2.67 (br. s., 1 H), 3.21 (d, J=10.1 Hz, 1 H), 3.72 (d, J=9.9 Hz, 1 H), 4.10 (s, 1H), 4.12 (dd, J=12.1, 4.0 Hz, 1 H), 4.45 (d, J=4.9 Hz, 1 H), 4.57 (d, J=12.3 Hz, 1 H), 4.87 (d, J=12.3 Hz, 1 H), 5.94 (s, 1 H), 6.16 (d, J=4.4 Hz, 1 H), 6.68 (br. s., 1 H), 7.02-7.10 (m, 1 H), 7.27-7.33 (m, 2 H), 7.34-7.39 (m, 2 H); LCMS (ESI) m/z: 485.3 (M+18).

Example 7

(((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl butylcarbamate

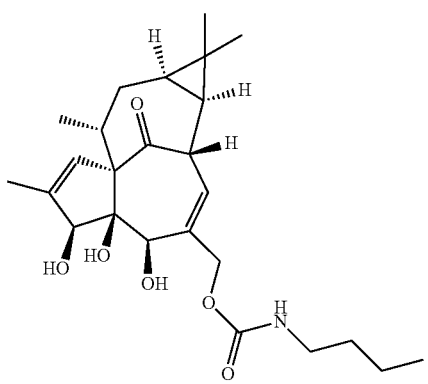 [SMILES: CCCCNC(=O)OCC1=C[C@@H]2C(=O)[C@]3(C=C(C)[C@H](O)[C@@]3(O)[C@@H]1O)[C@H](C)C[C@@H]1[C@H]2C1(C)C]

To a solution of ingenol (100 mg, 0.287 mmol) in dichloromethane (DCM) (2 mL) and N,N-dimethylformamide (DMF) (0.2 mL) at RT was added butyl isocyanate (0.039 mL, 0.344 mmol). After 3 hours 40 min, triethylamine (0.100 mL, 0.717 mmol) was added. After 18 hours, a mixture of carbamates was formed. The solvent was removed under reduced pressure. The crude was diluted with EtOAc (15 mL) and washed with water (2 mL). The organic phase was separated and concentrated under reduced pressure. The crude was purified by C18 column using an ISCO instrument [5-100% ACN gradient, 0.1% formic acid, 150 g ISCO C18 column]. ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl butylcarbamate (60.3 mg, 0.132 mmol, 46% yield) as white solid. $^1$H NMR (400 MHz, CHLOROFORM-d) δ ppm 0.65-0.77 (m, 1 H), 0.89-0.95 (m, 4 H), 0.97 (d, J=7.3 Hz, 3 H), 1.06 (s, 3 H), 1.11 (s, 3 H), 1.33 (dq, J=14.8, 7.2 Hz, 2 H), 1.46 (quin, J=7.2 Hz, 2 H), 1.76 (dt, J=15.6, 5.8 Hz, 1 H), 1.84 (s, 3 H), 2.27 (dd, J=15.5, 8.9 Hz, 1 H), 2.37 (br. s., 1 H), 2.96 (br. s., 1 H), 3.11-3.20 (m, 2 H), 3.65-3.75 (m, 2 H), 4.03 (s, 1 H), 4.09-4.18 (m, 1 H), 4.39-4.48 (m, 2 H), 4.70-4.82 (m, 2 H), 5.90 (s, 1 H), 6.09 (d, J=4.4 Hz, 1 H); LCMS(ESI) m/z: 448.4 (M+1).

Example 8

(((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl benzylcarbamate

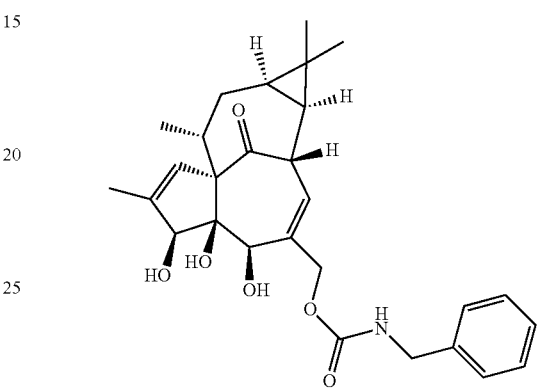

To a solution of ingenol (100 mg, 0.287 mmol) in N,N-dimethylformamide (DMF) (2 mL) was added triethylamine (0.100 mL, 0.717 mmol) and benzyl isocyanate (0.046 mL, 0.344 mmol) at RT. After 2 hours, a second batch of benzyl isocyanate (23 uL, 0.6 eq) was added. The mixture was stirred overnight to give a mixture of carbamates. The crude was purified by C18 using an ISCO instrument [15-60% ACN gradient over 20 min, 30 g ISCO gold column] to give impure product. This was further purified using silica gel column chromatography [20-70% EtOAc in hexanes, 12 g ISCO gold column] to give ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl benzylcarbamate (6.9 mg, 0.014 mmol, 4.7% yield) as white solid. $^1$H NMR (400 MHz, CHLOROFORM-d) δ ppm 0.65-0.75 (m, 1 H), 0.92-0.99 (m, 4 H), 1.06 (s, 3 H), 1.11 (s, 3 H), 1.76 (dt, J=15.7, 5.6 Hz, 1 H), 1.83 (s, 3 H), 2.27 (dd, J=15.5, 8.9 Hz, 1 H), 2.35 (br. s., 1 H), 2.87 (d, J=6.0 Hz, 1 H), 3.50 (d, J=9.9 Hz, 1 H), 3.68 (d, J=9.7 Hz, 1 H), 4.05 (s, 1H), 4.12 (d, J=8.1 Hz, 1 H), 4.35 (br. s., 2 H), 4.42 (d, J=5.9 Hz, 1 H), 4.51 (d, J=12.5 Hz, 1H), 4.79 (d, J=12.5 Hz, 1 H), 5.08 (br. s., 1 H), 5.90 (s, 1 H), 6.10 (d, J=2.9 Hz, 1 H), 7.27-7.39 (m, 5 H); LCMS(ESI) m/z: 482.4 (M+1).

Example 9

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl cyclohexyl (methyl)carbamate

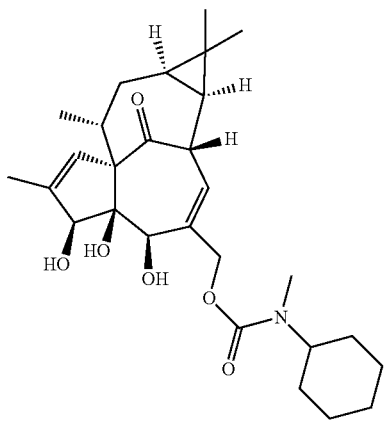 [SMILES: CC1=C[C@]23C(=O)[C@@H](C=C(COC(=O)N(C)C4CCCCC4)[C@@H](O)[C@]2(O)[C@H]1O)[C@H]1[C@@H](C[C@H]3C)C1(C)C]

Step 1: (1aR,2S,5R,5aS,6S,8aS,9R,10aR)-6-((diethyl(isopropyl)silyl)oxy)-4-(((diethyl(isopropyl)silyl)oxy)methyl)-5,5a-dihydroxy-1,1,7,9-tetramethyl-1a,2,5,5a,6,9,10,10a-octahydro-1H-2,8a-methanocyclopenta[a]cyclopropa[e][10]annulen-11-one To a solution of ingenol (1.5 g, 4.30 mmol) in N,N-dimethylformamide (DMF) (12.5 mL) at RT was added imidazole (4.69 g, 68.9 mmol) followed by chlorodiethyl (isopropyl)silane (4.77 mL, 25.8 mmol). After 1.5 hours, the mixture was diluted with EtOAc (200 mL) and washed with water (50 mL), then brine (50 mL), dried (Na$_2$SO$_4$), filtered and concentrated. The crude was absorbed on Celite® and purified by silica gel chromatography [5-100%(10% EtOAc in hexanes) in hexanes, 120 g ISCO column] to give (1aR,2S,5R,5aS,6S,8aS,9R,10aR)-6-((diethyl(isopropyl)silyl)oxy)-4-(((diethyl(isopropyl)silyl)oxy)methyl)-5,5a-dihydroxy-1,1,7,9-tetramethyl-1a,2,5,5a,6,9,10,10a-octahydro-1H-2,8a-methanocyclopenta[a]cyclopropa[e][10]annulen-11-one (2.2548 g, 3.73 mmol, 87% yield) followed by (1aR,2S,5R,5aR,6S,8aS,9R,10aR)-5-((diethyl(isopropyl)silyl)oxy)-4-(((diethyl(isopropyl)silyl)oxy)methyl)-5a,6-dihydroxy-1,1,7,9-tetramethyl-1a,2,5,5a,6,9,10,10a-octahydro-1H-2,8a-methanocyclopenta[a]cyclopropa[e][10]annulen-11-one (94.2 mg, 0.156 mmol, 3.62% yield) both isolated as white solid.

Data for (1aR,2S,5R,5aS,6S,8aS,9R,10aR)-6-((diethyl(isopropyl)silyl)oxy)-4-(((diethyl(isopropyl)silyl)oxy)methyl)-5,5a-dihydroxy-1,1,7,9-tetramethyl-1a,2,5,5a,6,9,10,10a-octahydro-1H-2,8a-methanocyclopenta[a]cyclopropa[e][10]annulen-11-one: $^1$H NMR (400 MHz, CHLOROFORM-d) δ ppm 0.58-0.79 (m, 9 H), 0.91-1.08 (m, 33H), 1.14 (s, 3 H), 1.74 (dt, J=15.6, 6.0 Hz, 1 H), 1.82 (d, J=1.1 Hz, 3 H), 2.23 (ddd, J=15.5, 8.1, 2.7 Hz, 1 H), 2.35-2.45 (m, 1 H), 3.27 (d, J=9.7 Hz, 1 H), 3.71 (d, J=9.5 Hz, 1 H), 3.88 (d, J=0.9 Hz, 1 H), 4.07 (m, J=11.7, 2.4 Hz, 1 H), 4.11-4.17 (m, 1 H), 4.25-4.31 (m, 1 H), 4.56 (s, 1 H), 5.90 (d, J=1.5 Hz, 1 H), 6.01 (d, J=2.7 Hz, 1 H); LCMS(ESI) m/z: 627.6 (M+Na).

Data for (1aR,2S,5R,5aR,6S,8aS,9R,10aR)-5-((diethyl(isopropyl)silyl)oxy)-4-(((diethyl(isopropyl)silyl)oxy)methyl)-5a,6-dihydroxy-1,1,7,9-tetramethyl-1a,2,5,5a,6,9,10,10a-octahydro-1H-2,8a-methanocyclopenta[a]cyclopropa[e][10]annulen-11-one: $^1$H NMR (400 MHz, CHLOROFORM-d) δ ppm 0.58-0.76 (m, 9 H), 0.79-1.12 (m, 32H), 1.18-1.28 (m, 4 H), 1.73 (ddd, J=16.0, 12.0, 6.6 Hz, 1 H), 1.83 (s, 3 H), 1.98 (d, J=15.0 Hz, 1 H), 2.48 (d, J=11.0 Hz, 1 H), 2.72 (ddd, J=11.9, 6.6, 2.4 Hz, 1 H), 3.59 (s, 1 H), 3.92 (d, J=10.8 Hz, 1 H), 4.05-4.16 (m, 2 H), 4.20 (s, 1 H), 4.72 (dd, J=10.2, 7.2 Hz, 1 H), 5.34 (s, 1 H), 6.18 (d, J=6.6 Hz, 1 H); LCMS(ESI) m/z: 627.6 (M+Na).

Step 2: (1aR,2S,5R,5aS,6S,8aS,9R,10aR)-6-((diethyl(isopropyl)silyl)oxy)-5,5a-dihydroxy-4-(hydroxymethyl)-1,1,7,9-tetramethyl-1a,2,5,5a,6,9,10,10a-octahydro-1H-2,8a-methanocyclopenta[a]cyclopropa[e][10]annulen-11-one To a solution of (1aR,2S,5R,5aS,6S,8aS,9R,10aR)-6-((diethyl(isopropyl)silyl)oxy)-4-(((diethyl(isopropyl)silyl)oxy)methyl)-5,5a-dihydroxy-1,1,7,9-tetramethyl-1a,2,5,5a,6,9,10,10a-octahydro-1H-2,8a-methanocyclopenta[a]cyclopropa[e][10]annulen-11-one (150 mg, 0.248 mmol) in THF (4 mL) at 0° C. (ice-water bath) was added triethylamine trihydrofluoride (0.202 mL, 1.240 mmol). After 80 min, sat. aq. NaHCO$_3$ (2 mL) was added to the mixture and extracted with EtOAc (20 mL, 10 mL). The organic extracts were dried (Na$_2$SO$_4$), filtered and concentrated. The crude was absorbed on Celite® and purified by silica gel chromatography [0-50% EtOAc in hexanes, 24 g ISCO gold column] to give (1aR,2S,5R,5aS,6S,8aS,9R,10aR)-6-((diethyl(isopropyl)silyl)oxy)-5,5a-dihydroxy-4-(hydroxymethyl)-1,1,7,9-tetramethyl-1a,2,5,5a,6,9,10,10a-octahydro-1H-2,8a-methanocyclopenta[a]cyclopropa[e][10]annulen-11-one (68 mg, 0.143 mmol, 57.5% yield) as foam. $^1$H NMR (400 MHz, CHLOROFORM-d) δ ppm 0.54-0.88 (m, 10 H), 0.93-1.10 (m, 18 H), 1.60-1.72 (m, 1 H), 1.76 (s, 3 H), 2.24 (dd, J=14.1, 9.3 Hz, 1 H), 2.40 (br. s., 1 H), 3.43 (d, J=8.8 Hz, 1 H), 3.82-3.98 (m, 3 H), 4.09 (d, J=11.4 Hz, 1 H), 4.49 (s, 1 H), 4.59 (br. s., 1 H), 5.11 (d, J=10.1 Hz, 1 H), 5.76 (s, 1 H), 5.85 (br. s., 1 H); LCMS(ESI) m/z: 477.5 (M+1).

Step 3: ((1aR,2S,5R,5aS,6S,8aS,9R,10aR)-6-((diethyl(isopropyl)silyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl cyclohexyl(methyl)carbamate To a solution of (1aR,2S,5R,5aS,6S,8aS,9R,10aR)-6-((diethyl(isopropyl)silyl)oxy)-5,5a-dihydroxy-4-(hydroxymethyl)-1,1,7,9-tetramethyl-1a,2,5,5a,6,9,10,10a-octahydro-1H-2,8a-methanocyclopenta[a]cyclopropa[e][10]annulen-11-one (66.8 mg, 0.140 mmol) in THF (2 mL) at 0° C. was added LHMDS, 1 M in THF (0.154 mL, 0.154 mmol). After 5 min, a solution of cyclohexyl(methyl)carbamic chloride (29.5 mg, 0.168 mmol) in THF (0.3 mL) was added dropwise. The mixture was allowed to warm to RT overnight. Brine (5 mL) was added and the mixture was extracted with EtOAc (40 mL). The organic phase was collected, dried (Na$_2$SO$_4$), filtered and concentrated. The crude was absorbed on Celite® and purified by silica gel chromatography [2-30% EtOAc in hexanes, then gradient to 100% EtOAc, 12 g ISCO gold column over 18 min] to give (((1aR,2S,5R,5aS,6S,8aS,9R,10aR)-6-((diethyl(isopropyl)silyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl) methyl cyclohexyl(methyl)carbamate (48.6 mg, 0.079 mmol, 56% yield) [LCMS(ESI) m/z: 614.6 (M-1)] followed by recovery of starting material (16.1 mg, 0.034 mmol, 24% yield) [LCMS(ESI) m/z: 475.6 (M-1)] both isolated as oil.

Step 4: ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl cyclohexyl(methyl)carbamate To a solution of ((1aR,2S,5R,5aS,6S,8aS,9R,10aR)-6-((diethyl(isopropyl)silyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl cyclohexyl(methyl)carbamate (48.6 mg, 0.079 mmol) in THF (2 mL) at 0° C. (ice-water bath) was added triethylamine trihydrofluoride (0.643 mL, 3.95 mmol). The mixture was allowed to warm to RT and stirred overnight. The crude was absorbed on Celite® and purified by column chromatography [10-100% EtOAc in hexanes, 4 g ISCO gold column] to give ((1aR,2S,5R,5aR,6S,8aS,9R,10aR)-5,5a,6-trihydroxy-1,1,7,9-tetramethyl-11-oxo-1a,2,5,5a,6,9,10,10-a-octahydro-1H-2,8a-methanocyclopenta[a]cyclopropa[e][10]annulen-4-yl)methyl cyclohexyl(methyl)carbamate (25.5 mg, 0.051 mmol, 64.3% yield) as white solid. $^1$H NMR (400 MHz, DMSO-d6) δ ppm 0.52-0.66 (m, 1 H), 0.77 (dd, J=11.8, 8.5 Hz, 1 H), 0.84 (d, J=7.0 Hz, 3 H), 1.02 (s, 3 H), 1.06 (s, 3 H), 1.09-1.46 (m, 5 H), 1.48-1.68 (m, 4 H), 1.70-1.82 (m, 5 H), 2.20-2.33 (m, 1 H), 2.38 (br. s., 1 H), 2.68 (s, 3 H), 3.43 (d, J=10.3 Hz, 1 H), 3.54-3.87 (m, 1 H), 4.09-4.17 (m, 1 H), 4.23 (d, J=5.9 Hz, 1 H), 4.42 (d, J=12.5 Hz, 1H), 4.55 (br. s., 1 H), 4.65 (s, 1 H), 5.07 (br. s., 1 H), 5.66 (s, 1 H), 5.74 (d, J=6.0 Hz, 1 H), 5.88 (br. s., 1 H); LCMS(ESI) m/z; 488.5 (M+1).

Example 10

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl indoline-1-carboxylate

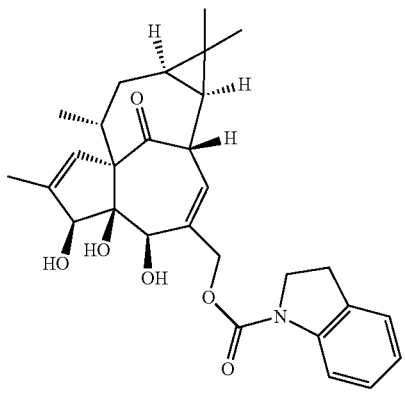 [SMILES: CC1=C[C@]23C(=O)[C@@H](C=C(COC(=O)N4CCc5ccccc54)[C@@H](O)[C@]2(O)[C@H]1O)[C@H]1[C@@H](C[C@H]3C)C1(C)C]

Example 11

(1aR,2S,5R,5aS,6S,8aS,9R,10aR)-5,5a-dihydroxy-4-(((indoline-1-carbonyl)oxy)methyl)-1,1,7,9-tetramethyl-11-oxo-1a,2,5,5a,6,9,10,10a-octahydro-1H-2,8a-methanocyclopenta[a]cyclopropa[e][10]annulen-6-yl indoline-1-carboxylate

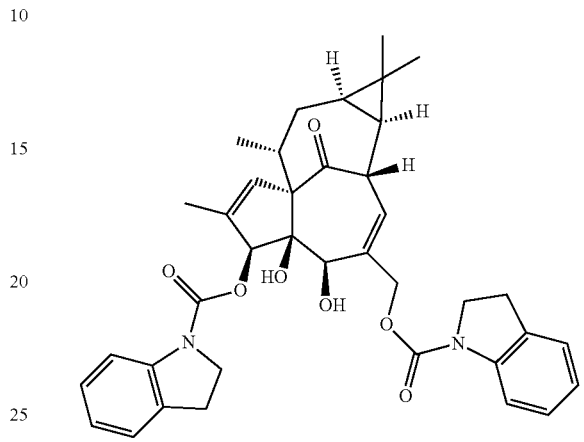

To a solution of ingenol (54.1 mg, 0.155 mmol) and potassium carbonate (64.4 mg, 0.466 mmol) in N,N-dimethylformamide (DMF) (1 mL) at 0° C. (ice-water bath) was added a solution of indoline-1-carbonyl chloride (28.2 mg, 0.155 mmol) in DCM (0.8 mL) over 5 minutes. The mixture was allowed to warm to RT and stir overnight to give a mixture of carbamates. The crude was filtered through 0.45 um PTFE Acrodisc and purified by C18 column chromatography [20-100% ACN gradient, 0.1% formic acid, 30 g ISCO C18 gold column]. ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl indoline-1-carboxylate (32.7 mg, 0.066 mmol, 42% yield) and (1aR,2S,5R,5aS,6S,8aS,9R,10aR)-5,5a-dihydroxy-4-(((indoline-1-carbonyl)oxy)methyl)-1,1,7,9-tetramethyl-11-oxo-1a,2,5,5a,6,9,10,10-a-octahydro-1H-2,8a-methanocyclopenta[a]cyclopropa[e][10]annulen-6-yl indoline-1-carboxylate (19.8 mg, 0.029 mmol, 19%) were isolated both as white solid.

Data for ((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl indoline-1-carboxylate: $^1$H NMR (400 MHz, DMSO-d6) δ ppm 0.56-0.65 (m, 1 H), 0.79 (dd, J=11.9, 8.4 Hz, 1 H), 0.85 (d, J=7.0 Hz, 3 H), 1.03 (s, 3 H), 1.07 (s, 3 H), 1.65 (dt, J=15.4, 5.6 Hz, 1 H), 1.73 (s, 3 H), 2.22-2.35 (m, 1 H), 2.40 (br. s., 1 H), 3.09 (t, J=8.5 Hz, 2H), 3.51 (d, J=9.2 Hz, 1 H), 3.93 (t, J=8.5 Hz, 2 H), 4.17 (d, J=9.0 Hz, 1 H), 4.25 (d, J=5.9 Hz, 1 H), 4.59 (d, J=12.8 Hz, 1 H), 4.68 (s, 1 H), 4.71 (br. s., 1 H), 5.20 (d, J=10.4 Hz, 1 H), 5.68 (br. s., 1 H), 5.75 (d, J=5.9 Hz, 1 H), 5.98 (br. s., 1 H), 6.93 (t, J=7.4 Hz, 1 H), 7.12 (br. s., 1 H), 7.21 (d, J=7.1 Hz, 1 H), 7.68 (br. s., 1 H); LCMS(ESI) m/z: 494.5 (M+1).

Data for (1aR,2S,5R,5aS,6S,8aS,9R,10aR)-5,5a-dihydroxy-4-(((indoline-1-carbonyl)oxy)methyl)-1,1,7,9-tetramethyl-11-oxo-1a,2,5,5a,6,9,10,10a-octahydro-1H-2,8a-methanocyclopenta[a]cyclopropa[e][10]annulen-6-yl indoline-1-carboxylate: $^1$H NMR (400 MHz, DMSO-d6) δ ppm 0.58-0.69 (m, 1 H), 0.81 (dd, J=11.7, 8.4 Hz, 1 H), 0.92 (d, J=7.0 Hz, 3 H), 1.03 (s, 3 H), 1.06 (s, 3 H), 1.67-1.85 (m, 4

H), 2.33 (br. s., 1 H), 2.57 (br. s., 1 H), 3.10 (t, J=8.5 Hz, 4 H), 3.62-3.79 (m, 1 H), 3.83-4.00 (m, 3 H), 4.10 (br. s., 1 H), 4.24 (d, J=8.8 Hz, 1 H), 4.58 (d, J=12.8 Hz, 1 H), 4.78 (d, J=11.0 Hz, 1 H), 5.44 (br. s., 1 H), 5.69 (br. s., 2 H), 5.95 (br. s., 1 H), 6.03 (br. s., 1 H), 6.94 (t, J=7.4 Hz, 2 H), 7.13 (br. s., 2 H), 7.21 (d, J=7.3 Hz, 2 H), 7.73 (br. s., 2 H); LCMS(ESI) m/z: 639.5 (M+1).

Example 12

(1aR,2S,5R,5aR,6S,8aS,9R,10aR)-5,5a,6-trihydroxy-1,1,7,9-tetramethyl-4-(((5-(trifluoromethyl)pyrimidin-2-yl)oxy)methyl)-1a,2,5,5a,6,9,10,10a-octahydro-1H-2,8a-methanocyclopenta[a]cyclopropa[e][10]annulen-11-one

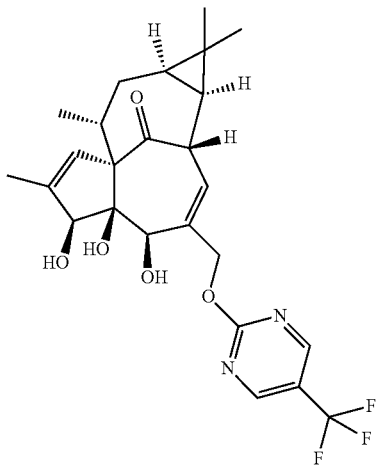 [SMILES: CC1=C[C@]23C(=O)[C@@H](C=C(COc4ncc(C(F)(F)F)cn4)[C@@H](O)[C@]2(O)[C@H]1O)[C@H]1[C@@H](C[C@H]3C)C1(C)C]

To a solution of ingenol (145 mg, 0.416 mmol) and 2-chloro-5-(trifluoromethyl)pyrimidine (76 mg, 0.416 mmol) in DMF (3 mL) at RT was added triethylamine (0.116 mL, 0.832 mmol). After 39.5 hours, the mixture was purified by C18 using an ISCO instrument [20-60% ACN gradient over 25 min, 30 g ISCO gold column] to give impure product which was further purified by silica gel chromatography [10-75% EtOAc in hexanes, 12 g ISCO column]. The fractions were concentrated and lyophilized from ACN/water to give (1aR,2S,5R,5aR,6S,8aS,9R,10aR)-5,5a,6-trihydroxy-1,1,7,9-tetramethyl-4-(((5-(trifluoromethyl)pyrimidin-2-yl)oxy)methyl)-1a,2,5,5a,6,9,10,10a-octahydro-1H-2,8a-methanocyclopenta[a]cyclopropa[e][10]annulen-11-one (10.8 mg, 0.021 mmol, 5% yield). $^1$H NMR (400 MHz, CHLOROFORM-d) δ ppm 0.65-0.76 (m, 1 H), 0.93-1.02 (m, 4 H), 1.06 (s, 3 H), 1.13 (s, 3 H), 1.73-1.83 (m, 1 H), 1.87 (s, 3 H), 2.22-2.39 (m, 2 H), 2.44 (d, J=5.1 Hz, 1 H), 2.97 (d, J=10.8 Hz, 1 H), 3.87 (d, J=10.3 Hz, 1 H), 4.10 (s, 1 H), 4.16 (d, J=11.5 Hz, 1H), 4.47 (d, J=6.0 Hz, 1 H), 4.91 (d, J=12.3 Hz, 1 H), 5.08 (d, J=12.1 Hz, 1 H), 5.96 (s, 1 H), 6.28 (d, J=4.0 Hz, 1 H), 8.75 (s, 2 H); LCMS(ESI) m/z: 495.3 (M+1).

ANTIVIRAL ASSAYS

For the Jurkat HIV Latency assay, compounds are dissolved and titrated in DMSO and diluted 100-fold in assay medium (RPMI-1640 containing 10% fetal bovine serum) containing an equal mixture of three HIV-infected Jurkat cell clones (C16, I15 and N6) at a total concentration of 1-2× 10e$^5$ cells/mL. To test stability, compounds are pre-incubated in an assay medium for 48 hours at 37° C. prior to adding cells (48 hr EC50). Compounds that induce HIV expression result in a dose-dependent production of the HIV expressed luciferase enzyme. After the incubation of cells with compound for 24 hours at 37° C., HIV activation and cytotoxicity are determined by measuring luminescence after the addition of Promega Steady-Glo® Luciferase Assay reagent or CellTiter-Glo® Luminescent Cell Viability Assay reagent, respectively.

Potency results from the above assay are set forth in Table 3.

| Example No. | EC$_{50}$ (nM) |
| --- | --- |
| 1 | 7 |
| 2 | 22 |
| 3 | 1109 |
| 4 | 4935 |
| 5 | 616 |
| 6 | 3678 |
| 7 | 1050 |
| 8 | 4333 |
| 9 | 50000 |
| 10 | 278 |
| 11 | 3500 |
| 12 | 5166 |

For the PBMC cytotoxicity assay, compounds are dissolved and titrated in DMSO and diluted 100-fold in assay medium (RPMI-1640 containing 10% fetal bovine serum) containing peripheral blood mononuclear cells (PBMCs) from healthy donors at a concentration of 4×10e$^5$ cells/mL. After the incubation of PBMCs with compound for 72 hours at 37° C., cytotoxicity is determined by measuring luminescence after the addition of Promega CellTiter-Glo® Luminescent Cell Viability Assay reagent.

What is claimed is:
1. A compound according to formula (II):

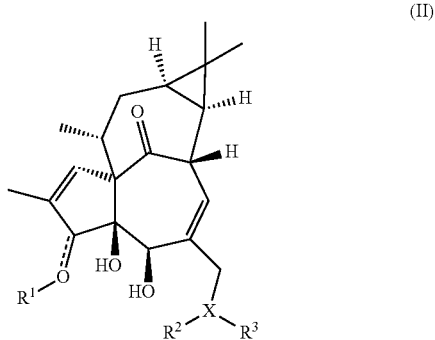

(II)

or a pharmaceutically acceptable salt thereof:
X is selected from O or N, wherein when X is O, then R$^3$ is absent;
R$^1$ is optionally present, and when present, the group:

is represented as:

and R₁ is —C(O)R⁴;

R² and R³ are independently selected from the group consisting of —H, methyl, —C(O)R¹⁰, —C(O)N(R⁶)₂, —S(O)₂CH₃, (C₆)heteroaryl and (C₉)heteroaryl, wherein when X is N, then R² and R³ may be taken together to form a pyrrolidine group optionally substituted by one or more R¹²;

R⁴ is —N(R⁶) R⁷;

R⁶ is methyl;

R⁷ is phenyl optionally substituted with one or more R¹³;

R¹⁰ is selected from the group consisting of (C₁-C₄)alkyl, (C₃-C₉)cyclohexyl, (C₅-C₆)heterocycle, and phenyl, wherein the cyclohexyl, (C₅-C⁶) heterocycle and phenyl are optionally substituted with one or more R¹¹; and wherein R¹¹, R¹² and R¹³ are independently selected from the group consisting of methyl, methoxy, oxo, trifluoromethyl and chloro;

with the proviso that when X is O and R² is H, R¹ is not present.

2. The compound according to claim 1, wherein R⁶ is methyl and R⁷ is aryl substituted by chloro.

3. The compound according to claim 1, wherein R² is —C(O)R¹⁰.

4. The compound according to claim 3, wherein R¹⁰ is aryl or methyl.

5. The compound according to claim 1, wherein X is N.

6. The compound according to claim 5, wherein R² and R³ together form a (C₂-C₉) heteroaryl.

7. The compound according claim 1, wherein R₁ is absent.

8. The compound according to claim 7, wherein X is O and R₂ is H.

9. A compound selected from the group consisting of:

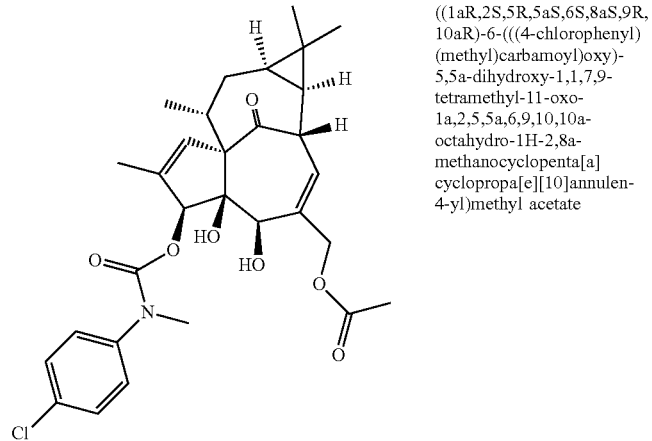

((1aR,2S,5R,5aS,6S,8aS,9R,10aR)-6-(((4-chlorophenyl)(methyl)carbamoyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl acetate

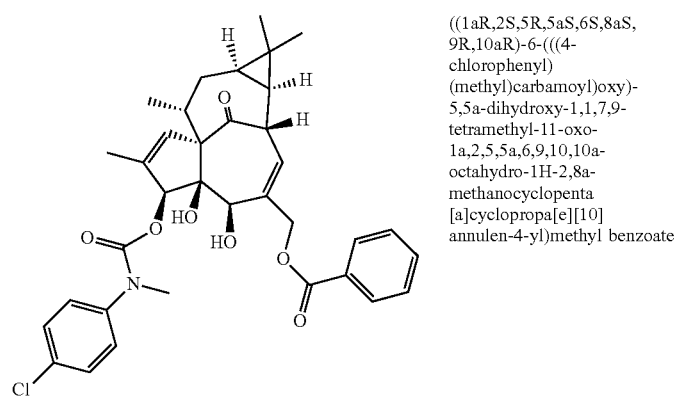

((1aR,2S,5R,5aS,6S,8aS,9R,10aR)-6-(((4-chlorophenyl)(methyl)carbamoyl)oxy)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl benzoate

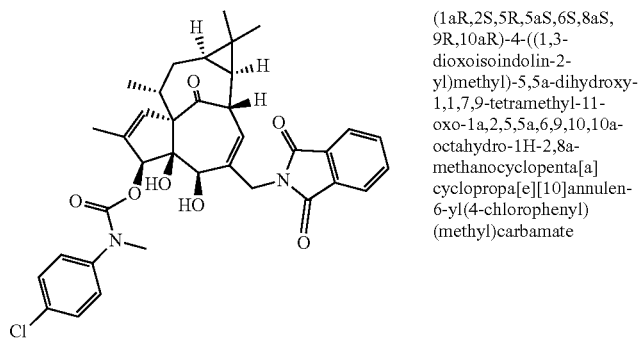
(1aR,2S,5R,5aS,6S,8aS,9R,10aR)-4-((1,3-dioxoisoindolin-2-yl)methyl)-5,5a-dihydroxy-1,1,7,9-tetramethyl-11-oxo-1a,2,5,5a,6,9,10,10a-octahydro-1H-2,8a-methanocyclopenta[a]cyclopropa[e][10]annulen-6-yl(4-chlorophenyl)(methyl)carbamate

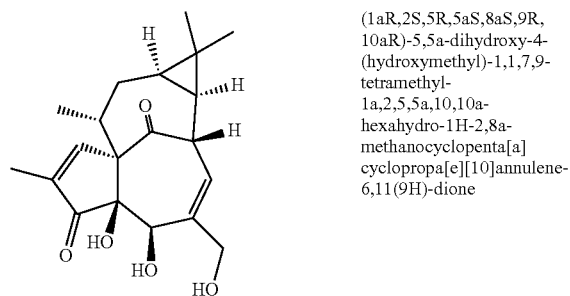
(1aR,2S,5R,5aS,8aS,9R,10aR)-5,5a-dihydroxy-4-(hydroxymethyl)-1,1,7,9-tetramethyl-1a,2,5,5a,10,10a-hexahydro-1H-2,8a-methanocyclopenta[a]cyclopropa[e][10]annulene-6,11(9H)-dione

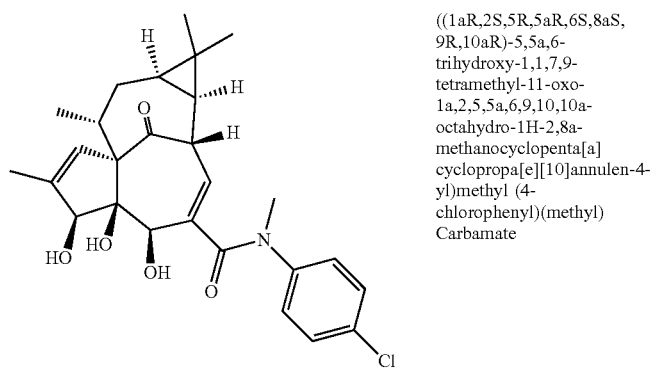
((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl (4-chlorophenyl)(methyl)Carbamate

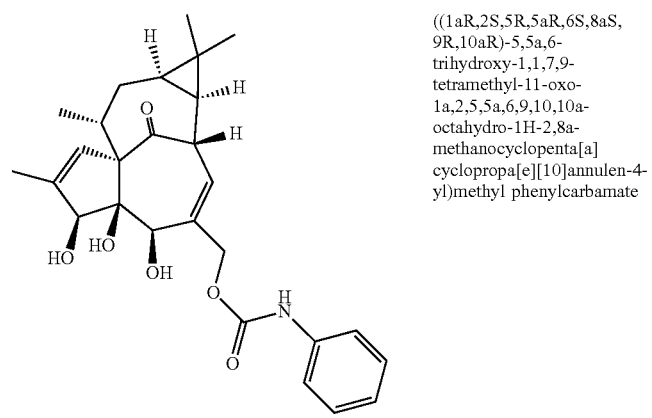
((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl phenylcarbamate

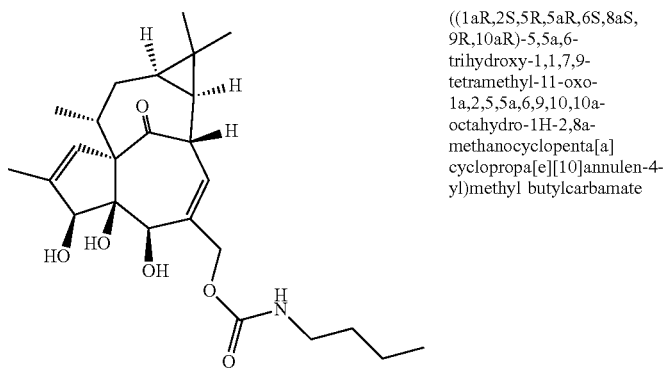

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl butylcarbamate

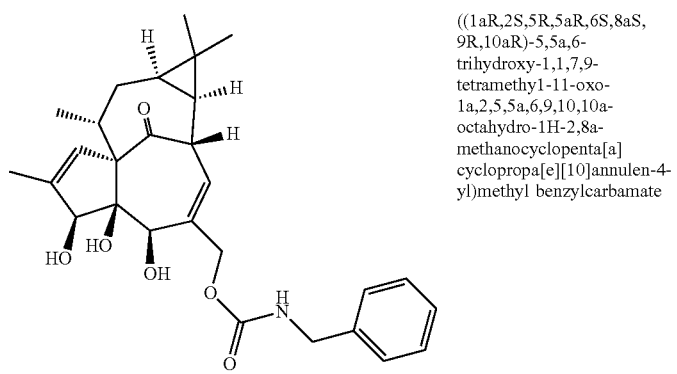

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl benzylcarbamate

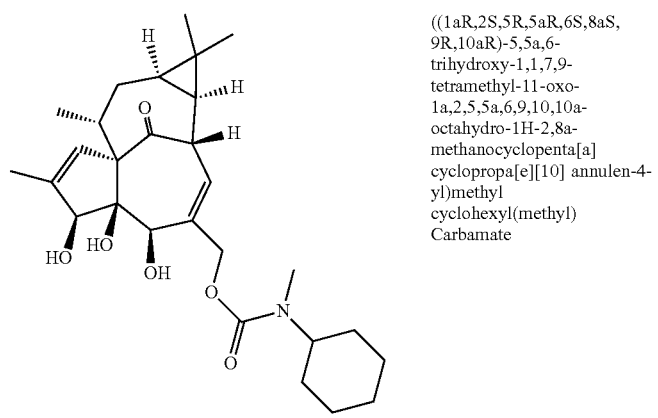

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10] annulen-4-yl)methyl cyclohexyl(methyl) Carbamate

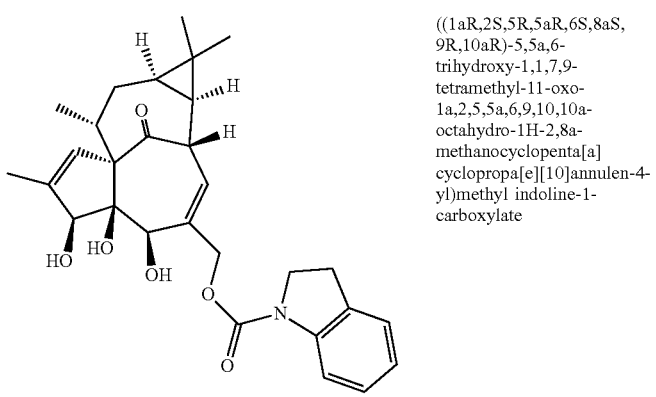

((1aR,2S,5R,5aR,6S,8aS,9R,10aR)-5,5a,6-trihydroxy-1,1,7,9-tetramethyl-11-oxo-1a,2,5,5a,6,9,10,10a-octahydro-1H-2,8a-methanocyclopenta[a]cyclopropa[e][10]annulen-4-yl)methyl indoline-1-carboxylate

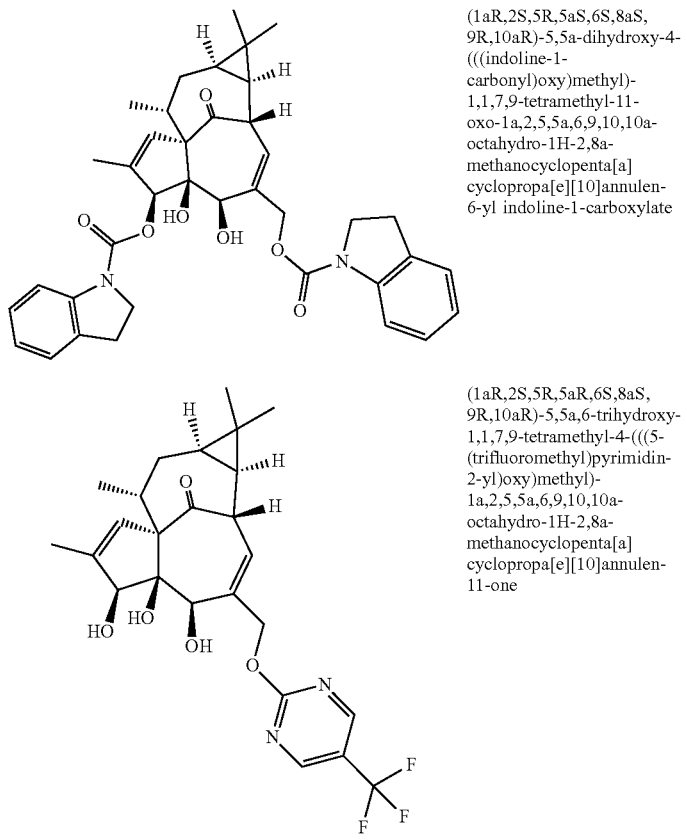

(1aR,2S,5R,5aS,6S,8aS,9R,10aR)-5,5a-dihydroxy-4-(((indoline-1-carbonyl)oxy)methyl)-1,1,7,9-tetramethyl-11-oxo-1a,2,5,5a,6,9,10,10a-octahydro-1H-2,8a-methanocyclopenta[a]cyclopropa[e][10]annulen-6-yl indoline-1-carboxylate (1aR,2S,5R,5aR,6S,8aS,9R,10aR)-5,5a,6-trihydroxy-1,1,7,9-tetramethyl-4-(((5-(trifluoromethyl)pyrimidin-2-yl)oxy)methyl)-1a,2,5,5a,6,9,10,10a-octahydro-1H-2,8a-methanocyclopenta[a]cyclopropa[e][10]annulen-11-one and pharmaceutically acceptable salts thereof.

10. A pharmaceutical composition comprising a compound according to claim 1, or a pharmaceutically acceptable salt thereof, and a pharmaceutically acceptable excipient.

11. The composition of claim 10, wherein the compound is present in an amorphous form.

12. The composition of claim 10, wherein the composition is in a tablet form.

13. The composition of claim 10, wherein the compound is present as a spray dried dispersion.

* * * * *